(12) United States Patent
Desharnais et al.

(10) Patent No.: US 11,078,521 B2
(45) Date of Patent: Aug. 3, 2021

(54) STABILIZATION OF NUCLEIC ACIDS ON PAPER

(71) Applicant: Biomatrica, Inc., San Diego, CA (US)

(72) Inventors: Joel Desharnais, La Mesa, CA (US); Daniela Roth, San Diego, CA (US); Vasco Liberal, San Diego, CA (US)

(73) Assignee: BIOMATRICA, INC., San Diego, CA (US)

( * ) Notice: Subject to any disclaimer, the term of this patent is extended or adjusted under 35 U.S.C. 154(b) by 79 days.

(21) Appl. No.: 16/343,886

(22) PCT Filed: Oct. 24, 2017

(86) PCT No.: PCT/US2017/058136
§ 371 (c)(1),
(2) Date: Apr. 22, 2019

(87) PCT Pub. No.: WO2018/081161
PCT Pub. Date: May 3, 2018

(65) Prior Publication Data
US 2019/0264257 A1 Aug. 29, 2019

Related U.S. Application Data

(60) Provisional application No. 62/411,996, filed on Oct. 24, 2016.

(51) Int. Cl.
| | |
|---|---|
| *C12Q 1/6806* | (2018.01) |
| *C12M 1/26* | (2006.01) |
| *C12M 1/00* | (2006.01) |
| *C12M 1/34* | (2006.01) |
| *C12Q 1/68* | (2018.01) |
| *C12Q 1/6809* | (2018.01) |
| *B01L 3/00* | (2006.01) |

(52) U.S. Cl.
CPC ............ *C12Q 1/6806* (2013.01); *C12M 1/00* (2013.01); *C12M 1/26* (2013.01); *C12M 1/34* (2013.01); *C12Q 1/68* (2013.01); *C12Q 1/6809* (2013.01); *B01L 3/5023* (2013.01)

(58) Field of Classification Search
CPC .............................. C12Q 1/6806; C12M 1/26
See application file for complete search history.

(56) References Cited

U.S. PATENT DOCUMENTS

| | | | |
|---|---|---|---|
| 4,970,171 A | 11/1990 | Messenger et al. | |
| 5,496,562 A * | 3/1996 | Burgoyne | C12N 15/1006 424/443 |
| 7,264,927 B2 * | 9/2007 | Nargessi | C12N 15/1006 435/6.16 |
| 8,519,125 B2 * | 8/2013 | Whitney | A01N 1/00 544/1 |
| 9,040,675 B2 * | 5/2015 | Bales | G01N 1/40 536/23.1 |
| 9,376,709 B2 | 6/2016 | Whitney et al. | |
| 2005/0227269 A1 * | 10/2005 | Lloyd, Jr. | B01L 3/50825 435/6.18 |
| 2012/0052572 A1 * | 3/2012 | Whitney | C12Q 1/6806 435/372 |
| 2013/0289265 A1 * | 10/2013 | Li | B01J 20/24 536/25.42 |
| 2014/0141411 A1 | 5/2014 | Lloyd, Jr. et al. | |
| 2014/0234942 A1 | 8/2014 | Kovacs et al. | |
| 2017/0067803 A1 * | 3/2017 | Jackson | A61B 5/150503 |

FOREIGN PATENT DOCUMENTS

| | | | |
|---|---|---|---|
| WO | WO 97/085547 | * | 3/1997 |
| WO | WO 2009/038853 A2 | | 3/2009 |
| WO | WO 2014/099121 A1 | | 6/2014 |
| WO | WO 2015/175672 A1 | | 11/2015 |
| WO | WO 2018/081161 A1 | | 5/2018 |

OTHER PUBLICATIONS

Marstokk et al., "Effect of Denaturant and Polymer Concentration on the Structural and Dynamical Properties of Aqueous Solutions of Poly(N-acetamido acrylamide)," (1998) *Macromolecules* 31 4205-4212.

Lim et al., "Direct and Indirect Models for Protein Chemical Denaturation are Characteristic of Opposite Dynamic Properties," (2016) *Department of Biological Sciences, Faculty of Science; National University of Singapore* 1-33.

Muller et al., "Preservation of Biospecimens at Ambient Temperature: Special Focus on Nucleic Acids and Opportunities for the Biobanking Community," (2016) *Biopreservation Today* 14:2 89-98.

Ru Choi et al., "An integrated paper-based sample-to-answer biosensor for nucleic acid testing at the point of care," (2016) *Lab Chip* 16:3 611-621.

(Continued)

*Primary Examiner* — Narayan K Bhat

(74) *Attorney, Agent, or Firm* — Casimir Jones, S.C.; Peter Schlueter

(57) ABSTRACT

The present invention and embodiments thereof relates to compositions and methods for storage, stabilization and preservation of biological samples and/or nucleic acids on a solid matrix. Methods for extracting, collecting, and recovering the biological samples and/or nucleic acids from the solid matrix are also described.

20 Claims, 5 Drawing Sheets

(56) References Cited

OTHER PUBLICATIONS

Dauner et al., "Evaluation of Nucleic Acid Stabilization Products for Ambient Temperature Shipping and Storage of Viral RNA and Antibody in a Dried Whole Blood Format," (2015) *American Journal of Tropical Medicine & Hygiene* 93:1 46-53.
Ishibashi M et al., "Is arginine a protein-denaturant," (2005) *Protein Expression and Purification, Academic Press* 42:1 1-6.
Extended European Search Report of EP Application No. 17865417.4 dated Apr. 28, 2020 (8 pages).
Int'l Search Report and Written Opinion of PCT/US2017/058136 dated Dec. 21, 2017 (7 pages).

* cited by examiner

STABILIZATION OF NUCLEIC ACIDS ON PAPER

CROSS-REFERENCE TO RELATED APPLICATION

This application claims priority under 35 U.S.C. § 119(e) to U.S. Provisional Patent Application No. 62/411,996, filed on Oct. 24, 2016, which is incorporated herein by reference in its entirety.

FIELD OF THE INVENTION

The present invention and embodiments thereof relates to compositions and methods for storage, stabilization and preservation of biological samples and/or nucleic acids on a solid matrix. Methods for extracting, collecting, and recovering the biological samples and/or nucleic acids from the solid matrix are also described.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Methods for storing, stabilizing and/or preserving the structural and functional integrity of nucleic acids is important for a wide variety of applications including diagnostic applications, therapeutic applications, prognostic applications, research applications, forensic applications, sequencing applications, amplification applications, analyte detection, sensing applications, etc. Various conditions such as pH, temperature, humidity, shipping, etc. can cause the degradation of nucleic acids. Therefore, there is an ongoing need for materials, compositions, and methods for storing, stabilizing, and/or preserving biological samples and/or nucleic acids.

For example, because of difficulties accessing rural cities in developing countries, it has been challenging to perform reliable prognosis of somebody's health when tests have to be performed with sophisticated equipment if the analytes to be analyzed are not stable. One such test is the determination of the presence of the human immunodeficiency virus (HIV) done by quantification of viral RNA in patient's clinical samples. This test can be performed with a single drop of blood or plasma deposited on a cellulosic paper where the material can then be shipped easily to diagnostic labs. However, the quantification of HIV RNA in clinical samples is challenging since viral RNA degrades rather rapidly especially at higher temperatures and humidity, conditions observed in countries such as those situated in the African continent. Therefore, modifying sample collection devices such as paper-based material to capture blood spots to allow greater stability of HIV RNA is of great need, allowing accurate diagnostic and evaluation of therapy efficacy in patients with low HIV viral load.

SUMMARY

The following embodiments and aspects thereof are described and illustrated in conjunction with systems, compositions, methods, and articles of manufacture which are meant to be exemplary and illustrative, not limiting in scope.

The present invention and embodiments thereof relates to compositions and methods for storage, stabilization and preservation of biological samples and/or nucleic acids on a solid matrix. Methods for extracting, collecting, and recovering the biological samples and/or nucleic acids from the solid matrix are also described.

In various embodiments, the present invention provides a solid matrix for storing a biological sample in a substantially dry state or a dry state, wherein the solid matrix comprises a matrix material and at least one buffer, wherein: the matrix material is a non-dissolvable dry solid material; the buffer is impregnated in the matrix material in a substantially dry state or a dry state; the solid matrix does not comprise a denaturant; and the biological sample comprises one or more nucleic acids. In some embodiments, the solid matrix further comprises at least one reducing agent, wherein the reducing agent is impregnated in the matrix material in a substantially dry state. In some embodiments, the reducing agent is dithiothreitol (DTT), 2-mercaptoethanol (2-ME), 2-mercaptoethylamine, or cysteine. In some embodiments, the solid matrix further comprises at least one antioxidant, wherein the antioxidant is impregnated in the matrix material in a substantially dry state. In some embodiments, the antioxidant is hydroquinone monomethyl ether (MEHQ), hydroquinone (HQ), or toluhydroquinone (THQ). In some embodiments, the non-dissolvable dry solid material is a cellulosic paper. In some embodiments, the buffer is selected from citric acid, tris(2-carboxyethyl)phosphine hydrochloride (TCEP-HCl), oxidized form of tris(2-carboxyethyl) phosphine hydrochloride (TCEPO-HCl), 2-amino-2-hydroxymethyl-propane-1,3-diol (Tris), 2-(N-morpholino) ethanesulfonic acid (MES), 3-(N-morpholino) propanesulfonic acid (MOPS), 4-(2-hydroxyethyl)-1-piperazineethanesulfonic acid (HEPES), phosphate buffers, acetic acid, ascorbic acid, sulfosalicylic acid, formic acid, glycine, glycine-glycine, malic acid, and succinic acid. In some embodiments, the buffer has a pH of 2.0 to 8.0. In some embodiments, the biological sample is blood, serum, plasma, tissue, saliva, cells, synovial fluids, urine, or semen. In some embodiments the buffer is citric acid.

In various embodiments the present invention provides a method for storing one or more biological samples on a solid matrix, comprising: contacting the solid matrix with a biological sample, wherein the biological sample comprises one or more nucleic acids; drying the solid matrix containing the biological sample; and storing the biological sample on the solid matrix in a substantially dry state or a dry state, wherein the solid matrix comprises a matrix material and at least one buffer, wherein: the matrix material is a non-dissolvable dry solid material; the buffer is impregnated in the matrix material in a substantially dry state or a dry state; and the solid matrix does not comprise a denaturant. In some embodiments, the method further comprises recovering the biological sample from the solid matrix. In some embodiments the method further comprises extracting the nucleic acids from the biological sample. In some embodiments the nucleic acids are extracted from the biological sample and stored on the solid matrix in a substantially dry state or a dry state. In some embodiments the method further comprises recovering the nucleic acids from the solid matrix. In some embodiments the non-dissolvable dry solid material is a cellulosic paper. In some embodiments the buffer is selected from citric acid, tris(2-carboxyethyl)phosphine hydrochloride (TCEP-HCl), oxidized form of tris(2-carboxyethyl) phosphine hydrochloride (TCEPO-HCl), 2-amino-2-hydroxymethyl-propane-1,3-diol (Tris), 2-(N-morpholino) ethanesulfonic acid (MES), 3-(N-morpholino) propanesulfonic acid (MOPS), 4-(2-hydroxyethyl)-1-piperazineethanesulfonic acid (HEPES), phosphate buffers, acetic acid, ascorbic acid, sulfosalicylic acid, formic acid, glycine, glycine-glycine, malic acid, and succinic acid. In some embodiments, the buffer has a pH of 2.0 to 8.0. In some embodiments the biological sample is blood, serum, plasma, tissue, saliva, cells, synovial fluids, urine, or semen. In some embodiments the nucleic acids are RNA. In some embodiments the nucleic acids are virus RNA. In some embodiments the buffer is citric acid.

BRIEF DESCRIPTION OF THE DRAWINGS

Exemplary embodiments are illustrated in referenced figures. It is intended that the embodiments and figures disclosed herein are to be considered illustrative rather than restrictive.

DETAILED DESCRIPTION OF THE INVENTION

Figure 1:
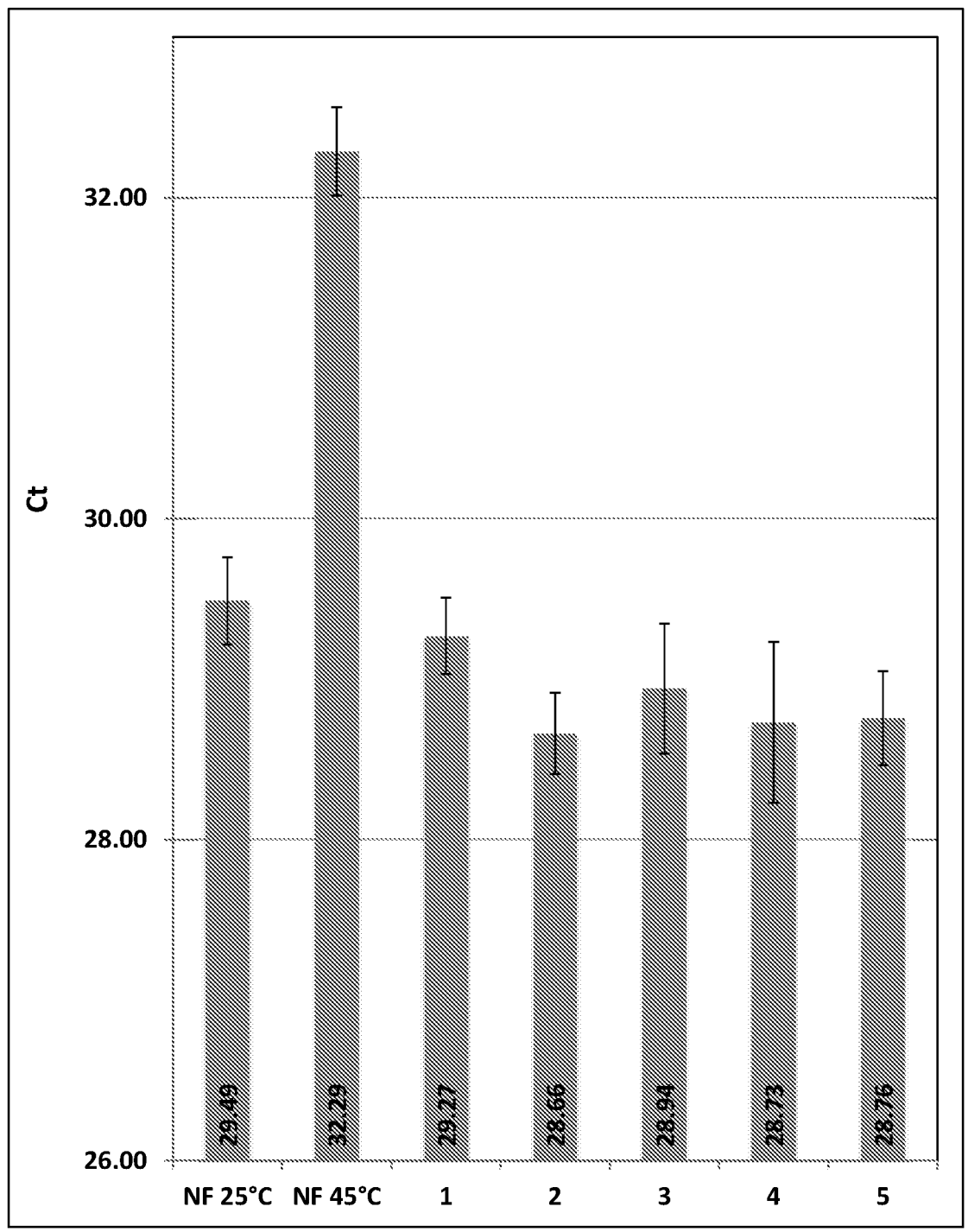
FIG. 1 depicts in accordance with various embodiments of the invention, HIV RNA recovery from Whatman® 903 paper stored at 25° C. and 45° C. for 30 days, where Ct (cycle thresholds) values for protected Whatman® 903 papers soaked in Formulations 1, 2, 3, 4, and 5 (Table 1) at 45° C. were compared with unprotected paper soaked in water (no formulation, NF 45° C.) and with unprotected paper soaked in water (no formulation, NF 25° C.).

All references cited herein are incorporated by reference in their entirety as though fully set forth. Unless defined otherwise, technical and scientific terms used herein have the same meaning as commonly understood by one of ordinary skill in the art to which this invention belongs.

One skilled in the art will recognize many methods and materials similar or equivalent to those described herein, which could be used in the practice of the present invention. Other features and advantages of the invention will become apparent from the following detailed description, taken in conjunction with the accompanying drawings, which illustrate, by way of example, various features of embodiments of the invention. Indeed, the present invention is in no way limited to the methods and materials described. For convenience, certain terms employed herein, in the specification, examples and appended claims are collected here.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

As used herein the term "comprising" or "comprises" is used in reference to compositions, methods, systems, articles of manufacture and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

"Optional" or "optionally" means that the subsequently described circumstance may or may not occur, so that the description includes instances where the circumstance occurs and instances where it does not.

Unless stated otherwise, the terms "a" and "an" and "the" and similar references used in the context of describing a particular embodiment of the application (especially in the context of claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. The abbreviation, "e.g." is derived from the Latin exempli gratia, and is used herein to indicate a non-limiting example. Thus, the abbreviation "e.g." is synonymous with the term "for example." No language in the specification should be construed as indicating any non-claimed element essential to the practice of the application.

The term "sample" or "biological sample" as used herein denotes a sample taken or isolated from a biological organism, e.g., a blood sample from a subject. Exemplary biological samples include, but are not limited to, cheek swab; mucus; whole blood, blood, serum; plasma; urine; saliva; semen; lymph; fecal extract; sputum; tears; other body fluid or biofluid; cell sample; tissue sample; tumor sample; and/or tumor biopsy etc. The term also includes a mixture of the above-mentioned samples. For example, the biological sample can be a mixture of blood and saliva; urine and fecal extract; mucus and a tissue sample; blood, saliva, and a tumor sample, etc. The term "sample" also includes untreated or pretreated (or pre-processed) biological samples. In some embodiments, a sample can comprise one or more cells from the subject. Additional biological samples include, but are not limited to physiological/pathological body liquids (e.g., secretions, excretions, exudates, and transudates) or cell suspensions (e.g., blood, lymph, synovial fluid, semen, saliva containing buccal cells, skin scrapings, hair root cells, etc.) of humans and animals; liquid extracts or homogenates of human or animal body tissues (e.g., bone, liver, kidney, etc.).

In some embodiments the biological sample is cheek swab; mucus; whole blood; blood; serum; plasma; synovial fluids; spinal fluid, cerebrospinal fluid, urine; saliva; semen; pre-ejaculate; vaginal fluids; breast milk; lymph; fecal extract; sputum; tears; other body fluid or biofluid; cells; cell sample; tissue; tissue sample; tumor; tumor sample; tumor biopsy; physiological/pathological body liquids (e.g., secretions, excretions, exudates, and transudates) or cell suspensions (e.g., blood, lymph, synovial fluid, semen, saliva containing buccal cells, skin scrapings, hair root cells, etc.) of humans and animals; or liquid extracts or homogenates of human or animal body tissues (e.g., bone, liver, kidney, etc.).

In some embodiments, the biological sample is blood, serum, plasma, tissue, saliva, cells, synovial fluids, urine, or semen. In some embodiments, the biological sample is blood. In some embodiments the biological sample is serum. In some embodiments the biological sample is plasma. In some embodiments the biological sample is tissue. In some embodiments the biological same is saliva. In some embodiments the biological sample is cells. In some embodiments the biological sample is synovial fluids. In some embodiments the biological sample is urine. In some embodiments the biological sample is semen.

In some embodiments, the biological sample is in a dry state or substantially dry state. In some embodiments, the biological sample is in a substantially dry state. In some embodiments, the biological sample is in a dry state.

The term "nucleic acid" refers without limitation to all forms of RNA (e.g., mRNA, miRNA, rRNA, tRNA, piRNA, ncRNA), DNA (e.g., genomic DNA, mtDNA), as well as recombinant RNA and DNA molecules or analogues of DNA or RNA generated using nucleotide analogues. The nucleic acid molecules can be single stranded or double stranded. Strands can include the coding or non-coding strand. Fragments of nucleic acids of naturally occurring RNA or DNA molecules are encompassed by the present invention and may be recovered using compositions and methods disclosed. The term "fragment" refers to a portion of the nucleic acid (e.g., RNA or DNA). The nucleic acid can be from any source including without limitation, animals, humans, plants, viruses, bacteria, fungi, plasmids, or parasites. In some embodiments, the nucleic acid is virus RNA. In some embodiments, the nucleic acid is human immunodeficiency virus (HIV) RNA (i.e., HIV RNA). In some embodiments, the nucleic acid is DNA and/or RNA or a combination thereof. In some embodiments, the nucleic acid is DNA (deoxyribonucleic acid). In some embodiments, the nucleic acid is RNA (ribonucleic acid).

In some embodiments, the nucleic acid is in a dry state or a substantially dry state. In some embodiments the nucleic acid is in a dry state. In some embodiments the nucleic acid is in a substantially dry state.

In some embodiments the nucleic acids are human nucleic acids (e.g., human DNA, human RNA, etc.) In some embodiments the nucleic acids are animal nucleic acids (e.g., animal DNA, animal RNA, etc.). In some embodiments the nucleic acids are infectious agent nucleic acids (e.g., infectious agent DNA, infectious agent RNA, etc.). Non-limiting examples of infectious agent nucleic acids include virus nucleic acids, bacteria nucleic acids, fungi nucleic acids, and parasite nucleic acids. In some embodiments the nucleic acids are virus nucleic acids (e.g., virus DNA, virus RNA, etc.). In some embodiments the nucleic acids are bacteria nucleic acids (e.g., bacteria DNA, bacteria RNA, etc.). In some embodiments the nucleic acids are fungus nucleic acids (e.g., fungus DNA, fungus RNA, etc.). In some embodiments the nucleic acids are parasite nucleic acids (e.g., parasite DNA, parasite RNA, etc.). In some embodiments the nucleic acids are plant nucleic acids (e.g., plant DNA, plant RNA, etc.).

The term "infectious agents" generally means anything that infiltrates another living organism. Non-limiting examples of infectious agents include viruses, bacteria, fungi, and parasites. In some embodiments the infectious agent is any one or more of viruses, bacteria, fungi, and/or parasites. In some embodiments the infectious agent is one or more viruses. In some embodiments the infectious agent is one or more bacteria. In some embodiments the infectious agent is one or more fungi. In some embodiments the infectious agent is one or more parasites.

Non-limiting examples of viruses include human immunodeficiency virus (HIV), human papillomavirus (HPV), hepatitis virus, ebolavirus, zika virus, west nile virus, dengue virus, rotavirus, influenza virus, measles virus, poliovirus, yellow fever virus, herpes virus, varicella zoster virus, and rabies virus.

Non-limiting examples of bacteria include *Clostridium tetani, Vibrio cholerae, Mycobacterium tuberculosis, Yersinia pestis, Streptococcus pneumoniae, Treponema pallidium, Neisseria gonorrhoeae, Salmonella typhi, Legionella pneumophila, Bacillus anthracis, Clostridium difficile, Mycobacterium leprae,* and *Mycobacterium lepromatosis.*

Non-limiting examples of parasites include *Plasmodium* type, *Entamoeba histolytica, Trichomonas vaginalis, Toxoplasma gondii, Trypanosoma cruzi, Trypanosoma brucei gambiense, Trypanosoma brucei rhodesiense, Taenia solium, Ancylostoma duodenale, Necator americanus, Enterobius vermicularis, Strongyloides, Trichinella, Dracunculus medinensis, Pediculus humanus capitis,* and *Pediculus humanus corporis.*

Non-limiting examples of fungi include yeasts of the genus *Candida, Candida auris, Cryptococcus, Histoplasma, Blastomyces, Coccidioides, Aspergillus, Trichophyton, Epidermophyton, Microsporum, Trichophyton rubrum,*

*Fusarium, Rhizopus* species, *Mucor* species, *Cunninghamella bertholletiae*, *Apophysomyces* species, *Lichtheimia* species, *Blastomyces, Coccidioides, Histoplasma*, and *Sporothrix*.

Additionally, biological samples can comprise various biological materials, including without limitation nucleic acids, proteins, viruses, bacteria, parasites, infectious agents, prions, stem cells, etc. Additional biological materials include, but are not limited to, physiological/pathological extracts or cell suspensions of plants; liquid products, extracts or suspensions of bacteria, fungi, plasmids, viruses, parasites, etc; liquid products, extracts or suspension of parasites including helminthes, protozonas, spirochetes, etc.; infectious agents; bacteria, viruses, fungi, or parasites.

Additionally, biological samples can comprise combinations from various sources, non-limiting examples include human blood or human plasma containing human nucleic acids; blood or plasma containing infectious agents; human blood or plasma containing viruses, bacteria, fungi, or parasites; human blood or plasma containing virus nucleic acids such as virus RNA (e.g., HIV RNA); animal fecal extract containing bacteria nucleic acids such as bacteria DNA and/or RNA; human blood from one subject mixed with human blood from a different subject; semen containing infectious agent nucleic acids, etc.

In various embodiments, the biological sample comprises one or more nucleic acids. In some embodiments, the nucleic acids are any one or more of human nucleic acids, animal nucleic acids, and/or infectious agent nucleic acids. In some embodiments the nucleic acids are any one or more of human nucleic acids and/or infectious agent nucleic acids. In some embodiments the nucleic acids are any one or more of animal nucleic acids and/or infectious agent nucleic acids. In some embodiments the nucleic acids are human nucleic acids. In some embodiments the nucleic acids are animal nucleic acids. In some embodiments the nucleic acids are infectious agent nucleic acids. In some embodiments the nucleic acids are any one or more of human nucleic acids, animal nucleic acids, virus nucleic acids, bacteria nucleic acids, fungus nucleic acids, and/or parasite nucleic acids. In some embodiments the nucleic acids are any one or more of human nucleic acids, virus nucleic acids, bacteria nucleic acids, fungus nucleic acids, and/or parasite nucleic acids. In some embodiments the nucleic acids are any one or more of animal nucleic acids, virus nucleic acids, bacteria nucleic acids, fungus nucleic acids, and/or parasite nucleic acids. In some embodiments, the nucleic acids are any one or more of human nucleic acids and/or virus nucleic acids. In some embodiments the nucleic acids are any one or more of human nucleic acids and/or bacteria nucleic acids. In some embodiments the nucleic acids are any one or more of human nucleic acids and/or fungus nucleic acids. In some embodiments the nucleic acids are any one or more of human nucleic acids and/or parasite nucleic acids. In some embodiments, the nucleic acids are any one or more of animal nucleic acids and/or virus nucleic acids. In some embodiments the nucleic acids are any one or more of animal nucleic acids and/or bacteria nucleic acids. In some embodiments the nucleic acids are any one or more of animal nucleic acids and/or fungus nucleic acids. In some embodiments the nucleic acids are any one or more of animal nucleic acids and/or parasite nucleic acids.

In some embodiments, the biological sample comprises one or more infectious agents, wherein the infectious agents comprise one or more nucleic acids. In some embodiments, the biological sample comprises one or more infectious agents; and one or more nucleic acids, wherein the nucleic acids are any one or more of animal nucleic acids and/or infectious agent nucleic acids. In some embodiments, the biological sample comprises one or more infectious agents; and one or more nucleic acids, wherein the nucleic acids are any one or more of human nucleic acids and/or infectious agent nucleic acids.

In some embodiments, the biological sample comprises one or more viruses; and one or more nucleic acids, wherein the nucleic acids are any one or more of human nucleic acids and/or virus nucleic acids. In some embodiments, the biological sample comprises one or more bacteria; and one or more nucleic acids, wherein the nucleic acids are any one or more of human nucleic acids and/or bacteria nucleic acids. In some embodiments, the biological sample comprises one or more fungi; and one or more nucleic acids, wherein the nucleic acids are any one or more of human nucleic acids and/or fungus nucleic acids. In some embodiments, the biological sample comprises one or more parasites; and one or more nucleic acids, wherein the nucleic acids are any one or more of human nucleic acids and/or parasite nucleic acids.

In some embodiments, the biological sample comprises one or more viruses; and one or more nucleic acids, wherein the nucleic acids are any one or more of animal nucleic acids and/or virus nucleic acids. In some embodiments, the biological sample comprises one or more bacteria; and one or more nucleic acids, wherein the nucleic acids are any one or more of animal nucleic acids and/or bacteria nucleic acids. In some embodiments, the biological sample comprises one or more fungi; and one or more nucleic acids, wherein the nucleic acids are any one or more of animal nucleic acids and/or fungus nucleic acids. In some embodiments, the biological sample comprises one or more parasites; and one or more nucleic acids, wherein the nucleic acids are any one or more of animal nucleic acids and/or parasite nucleic acids.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, and canine species, e.g., dog, fox, wolf. The terms, "patient", "individual" and "subject" are used interchangeably herein. In some embodiments, the subject is mammal. The mammal can be a human, non-human primate, mouse, rat, dog, cat, horse, or cow, but are not limited to these examples. In addition, the methods described herein can be used to treat domesticated animals and/or pets. In some embodiments, the subject is an animal. In some embodiments, the subject is a human.

"Mammal" as used herein refers to any member of the class Mammalia, including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term. In some embodiments the mammal is a human.

The term "extraction" refers to any method for releasing, separating and/or isolating the nucleic acids from a sample (e.g., a biological sample). In one embodiment, without being bound by theory, nucleic acids such as RNA and DNA can be extracted, for example, during evaporative sample cell lysis in the air or by contact with the matrix material or the presence of compounds in a matrix material and/or solid matrix (e.g., chemically modified solid matrix) that upon contact with the samples results in cell lysis and the release of nucleic acids. One of skill in the art will appreciate that any method that results in the extraction of nucleic acids, for example RNA, from a sample (e.g., plasma, blood, serum, tissue, saliva, cells, synovial fluids, urine, semen, etc.) such that the nucleic acids can be captured on the matrix material and/or solid matrix for storage, stabilization, and/or preservation of the nucleic acids may be used in the disclosed compositions and methods. In another embodiment, without being bound by theory, nucleic acids such as RNA and DNA can be extracted, for example, from a sample (e.g., a biological sample) subsequent to removal of the sample from the matrix material and/or solid matrix using any known method or technique. For example, any method that results in the extraction of nucleic acids, for example RNA, from a sample (e.g., a biological sample) may be employed. For example, any manual method or automated method that results in the extraction of nucleic acids, for example RNA, from a sample (e.g., a biological sample) may be employed.

In another embodiment, without being bound by theory, infectious agent nucleic acids, wherein an infectious agent is present in a biological sample, can be extracted, for example from the infectious agent during lysis in the air or by contact with the matrix material or the presence of compounds in a matrix material and/or solid matrix material (e.g., chemically modified solid matrix) that upon contact with the biological sample and/or the infectious agent therein results in release of the nucleic acids from the infectious agent. In another embodiment, without being bound by theory, infectious agent nucleic acids, wherein an infectious agent is present in a biological sample, can be extracted, for example from the infectious agent and/or biological sample subsequent to removal of the infectious agent and/or biological sample from the matrix material and/or solid matrix using any known method or technique. In some embodiments, the infectious agent is any one or more of viruses, bacteria, fungi, or parasites. In some embodiments the infectious agent nucleic acids are any one or more of virus nucleic acids, bacteria nucleic acids, fungi nucleic acids, and/or parasite nucleic acids.

The term "recovery" means obtaining the nucleic acid from the matrix material and/or solid matrix. In some embodiments, the methods comprise recovering one or more nucleic acids from the matrix material and/or solid matrix. In some embodiments, the nucleic acids are recovered from the matrix material and/or solid matrix by a solid phase extraction technique. In some embodiments, the nucleic acids are recovered from the matrix material and/or solid matrix by rehydrating the solid matrix in a solvent, an aqueous solution, a buffer (or buffer solution), an organic solution, or combination thereof. In some embodiments, the recovered nucleic acids are subjected to further analysis.

The terms "storage" or "preservation" may be used interchangeably herein with respect to maintaining the biological sample and/or extracted nucleic acids in a format suitable for further analysis. As used herein, the terms "storing", "storage", "stored" and other derivatives of "store", when referring to a biological sample in dry or substantially dry form entrained to the dry or substantially dry stabilized solid matrix, means the preservation of the biological sample and the contents of the biological sample (e.g., nucleic acids) in a form suitable for subsequent analysis and which has not undergone substantial degradation. The time period for which the dried stabilized solid matrix treated with the biological sample may be stored according to the invention may be as short as the time necessary to transport the biological sample from the place of collection of the biological sample to the place where subsequent analysis is to be performed. The conditions under which the dried stabilized solid matrix treated with the biological sample may be stored varies. Typically, samples are stored at temperatures from −200° C. to 60° C., −150° C. to 60° C., −100° C. to 60° C., −50° C. to 60° C., −25° C. to 60° C., −10° C. to 60° C.; 0° C. to 60° C., 0° C. to 50° C., 0° C. to 40° C., 0° C. to 30° C., 5° C. to 60° C., 5° C. to 50° C., 5° C. to 40° C., 5° C. to 30° C., 10° C. to 60° C., 10° C. to 50° C., 10° C. to 40° C., 10° C. to 30° C., 15° C. to 60° C., 15° C. to 50° C., 15° C. to 40° C., 15° C. to 30° C., 20° C. to 60° C., 20° C. to 50° C., 20° C. to 40° C., 20° C. to 30° C., or 20° C. to 25. In some embodiments, samples are stored at 15° C. to 30° C.

In addition, dried stabilized solid matrix treated with the biological sample may optionally be stored in dry or desiccated conditions and/or under an inert atmosphere.

In addition, dried stabilized solid matrix treated with the biological sample may optionally be stored at ambient conditions, where the temperature (e.g., ambient temperature) and/or humidity (e.g., relative humidity) may vary depending on the environment. In addition, dried stabilized solid matrix treated with the biological sample may optionally be stored at ambient temperature.

The term "ambient temperature" refers to a temperature having a range of 0° C. to 60° C. In some embodiments, ambient temperature is 0° C. to 60° C., 0° C. to 50° C., 0° C. to 40° C., 0° C. to 30° C., 10° C. to 60° C., 10° C. to 50° C., 10° C. to 40° C., 10° C. to 30° C., 15° C. to 30° C., 20° C. to 60° C., 20° C. to 50° C., 20° C. to 40° C., 20° C. to 30° C., 30° C. to 60° C., 30° C. to 50° C., 30° C. to 40° C., 40° C. to 60° C., 40° C. to 50° C., or 50° C. to 60° C. In some embodiments, ambient temperature is room temperature. In some embodiments, ambient temperature is 15° C. to 30° C.

In various embodiments, the relative humidity is in the range of 1% to 100%. In some embodiments, the relative humidity is 1% to 10%, 1% to 20%, 1% to 30%, 1% to 40%, 1% to 50%, 1% to 60%, 1% to 70%, 1% to 80%, 1% to 90%, 1% to 100%, 10% to 20%, 10% to 30%, 10% to 40%, 10% to 50%, 10% to 60%, 10% to 70%, 10% to 80%, 10% to 90%, 10% to 100%, 20% to 30%, 20% to 40%, 20% to 50%, 20% to 60%, 20% to 70%, 20% to 80%, 20% to 90%, 20% to 100%, 30% to 40%, 30% to 50%, 30% to 60%, 30% to 70%, 30% to 80%, 30% to 90%, 30% to 100%, 40% to 50%, 40% to 60%, 40% to 70%, 40% to 80%, 40% to 90%, 40% to 100%, 50% to 60%, 50% to 70%, 50% to 80%, 50% to 90%, 50% to 100%, 60% to 70%, 60% to 80%, 60% to 90%, 60% to 100%, 70% to 80%, 70% to 90%, 70% to 100%, 80% to 90%, 80% to 100%, 90% to 100%.

The term "reducing agent" as used herein refers to a chemical species that provides electrons to another chemical species. A variety of reducing agents are known in the art. Non-limiting examples of reducing agents that can be used in the various embodiments of the compositions and methods of the present invention include dithiothreitol (DTT), 2-mercaptoethanol (2-ME), 2-mercaptoethylamine, and cysteine. In some embodiments, the reducing agent is one or more of dithiothreitol (DTT), 2-mercaptoethanol (2-ME), 2-mercaptoethylamine, and/or cysteine. In some embodiments, the reducing agent is dithiothreitol (DTT), 2-mercaptoethanol (2-ME), 2-mercaptoethylamine, or cysteine. In some embodiments the reducing agent is dithiothreitol (DTT). In some embodiments the reducing agent is 2-mercaptoethanol (2-ME). In some embodiments the reducing agent is 2-mercaptoethylamine. In some embodiments the reducing agent is cysteine. Moreover, any combination of these or other reducing agents known in the art may be used to practice the invention.

The present invention is not limited to any specific concentration of the reducing agent. In various embodiments, the concentration of the reducing agent suitable for use with the present invention (e.g., compositions, methods, kits, solid matrices, matrix materials, formulations, etc.) is 1 mM-200 mM.

In various embodiments, the reducing agent has a concentration of 1 mM-200 mM. In various embodiments, the reducing agent has a concentration of 1 mM-200 mM, 1 mM-175 mM, 1 mM-150 mM, 1 mM-125 mM, 1 mM-100 mM, 1 mM-75 mM, 1 mM-50 mM, 1 mM-25 mM, 1 mM-10 mM, 10 mM-200 mM, 10 mM-175 mM, 10 mM-150 mM, 10 mM-125 mM, 10 mM-100 mM, 10 mM-75 mM, 10 mM-50 mM, 10 mM-25 mM, 20 mM-200 mM, 20 mM-175 mM, 20 mM-150 mM, 20 mM-125 mM, 20 mM-100 mM, 20 mM-75 mM, or 20 mM-50 mM.

In various embodiments, the concentration of the reducing agent is 1 mM to 150 mM. In various embodiments, the concentration of the reducing agent is 1 mM to 100 mM. In various embodiments, the concentration of the reducing agent is 1 mM to 80 mM. In various embodiments, the concentration of the reducing agent is 1 mM to 60 mM.

In various embodiments, the concentration of the reducing agent is 10 mM to 150 mM. In various embodiments, the concentration of the reducing agent is 10 mM to 100 mM. In various embodiments, the concentration of the reducing agent is 10 mM to 80 mM. In various embodiments, the concentration of the reducing agent is 10 mM to 60 mM.

In various embodiments, the concentration of the reducing agent is 20 mM to 150 mM. In various embodiments, the concentration of the reducing agent is 20 mM to 100 mM. In various embodiments, the concentration of the reducing agent is 20 mM to 80 mM. In various embodiments, the concentration of the reducing agent is 20 mM to 60 mM.

Non-limiting examples of a buffer are citric acid, tris(2-carboxyethyl)phosphine hydrochloride (TCEP-HCl), oxidized form of tris(2-carboxyethyl)phosphine hydrochloride (TCEPO-HCl), 2-amino-2-hydroxymethyl-propane-1,3-diol (Tris), 2-(N-morpholino)ethanesulfonic acid (MES), 3-(N-morpholino)propanesulfonic acid (MOPS), 4-(2-hydroxyethyl)-1-piperazineethanesulfonic acid (HEPES), tartaric acid, a phosphate buffer, acetic acid, ascorbic acid, sulfosalicylic acid, formic acid, glycine, glycine-glycine, malic acid, or succinic acid, or any combination thereof. Moreover, any combination of these or other buffers known in the art may be used to practice the invention.

In various embodiments of the present invention, the buffer is citric acid, tris(2-carboxyethyl)phosphine hydrochloride (TCEP-HCl), oxidized form of tris(2-carboxyethyl) phosphine hydrochloride (TCEPO-HCl), 2-amino-2-hydroxymethyl-propane-1,3-diol (Tris), 2-(N-morpholino)ethanesulfonic acid (MES), 3-(N-morpholino)propanesulfonic acid (MOPS), 4-(2-hydroxyethyl)-1-piperazineethanesulfonic acid (HEPES), tartaric acid, a phosphate buffer, acetic acid, ascorbic acid, sulfosalicylic acid, formic acid, glycine, glycine-glycine, malic acid, or succinic acid, or any combination thereof.

In some embodiments, the buffer is citric acid, tris(2-carboxyethyl)phosphine hydrochloride (TCEP-HCl), oxidized form of tris(2-carboxyethyl)phosphine hydrochloride (TCEPO-HCl), 2-amino-2-hydroxymethyl-propane-1,3-diol (Tris), 2-(N-morpholino)ethanesulfonic acid (MES), 3-(N-morpholino)propanesulfonic acid (MOPS), 4-(2-hydroxyethyl)-1-piperazineethanesulfonic acid (HEPES), tartaric acid, a phosphate buffer, acetic acid, ascorbic acid, sulfosalicylic acid, formic acid, glycine, glycine-glycine, malic acid, or succinic acid.

In some embodiments, the buffer is selected from any one or more of citric acid, tris(2-carboxyethyl)phosphine hydrochloride (TCEP-HCl), oxidized form of tris(2-carboxyethyl) phosphine hydrochloride (TCEPO-HCl), 2-amino-2-hydroxymethyl-propane-1,3-diol (Tris), 2-(N-morpholino)ethanesulfonic acid (MES), 3-(N-morpholino)propanesulfonic acid (MOPS), 4-(2-hydroxyethyl)-1-piperazineethanesulfonic acid (HEPES), tartaric acid, a phosphate buffer, acetic acid, ascorbic acid, sulfosalicylic acid, formic acid, glycine, glycine-glycine, malic acid, or succinic acid.

In some embodiments the two different buffers are selected from citric acid, tris(2-carboxyethyl)phosphine hydrochloride (TCEP-HCl), oxidized form of tris(2-carboxyethyl)phosphine hydrochloride (TCEPO-HCl), 2-amino-2-hydroxymethyl-propane-1,3-diol (Tris), 2-(N-morpholino)ethanesulfonic acid (MES), 3-(N-morpholino)propanesulfonic acid (MOPS), 4-(2-hydroxyethyl)-1-piperazineethanesulfonic acid (HEPES), tartaric acid a phosphate buffer, acetic acid, ascorbic acid, sulfosalicylic acid, formic acid, glycine, glycine-glycine, malic acid and succinic acid.

In some embodiments, the buffer is citric acid, tris(2-carboxyethyl)phosphine hydrochloride (TCEP-HCl), oxidized form of tris(2-carboxyethyl)phosphine hydrochloride (TCEPO-HCl), 2-amino-2-hydroxymethyl-propane-1,3-diol (Tris), 2-(N-morpholino)ethanesulfonic acid (MES), 3-(N-morpholino)propanesulfonic acid (MOPS), 4-(2-hydroxyethyl)-1-piperazineethanesulfonic acid (HEPES), a phosphate buffer, acetic acid, ascorbic acid, sulfosalicylic acid, formic acid, glycine, glycine-glycine, malic acid, or succinic acid, or any combination thereof.

In some embodiments, the buffer is citric acid, tris(2-carboxyethyl)phosphine hydrochloride (TCEP-HCl), oxidized form of tris(2-carboxyethyl)phosphine hydrochloride (TCEPO-HCl), 2-amino-2-hydroxymethyl-propane-1,3-diol (Tris), 2-(N-morpholino)ethanesulfonic acid (MES), 3-(N-morpholino)propanesulfonic acid (MOPS), 4-(2-hydroxyethyl)-1-piperazineethanesulfonic acid (HEPES), a phosphate buffer, acetic acid, ascorbic acid, sulfosalicylic acid, formic acid, glycine, glycine-glycine, malic acid, or succinic acid.

In some embodiments, the buffer is selected from any one or more of citric acid, tris(2-carboxyethyl)phosphine hydrochloride (TCEP-HCl), oxidized form of tris(2-carboxyethyl) phosphine hydrochloride (TCEPO-HCl), 2-amino-2-hydroxymethyl-propane-1,3-diol (Tris), 2-(N-morpholino)ethanesulfonic acid (MES), 3-(N-morpholino)propanesulfonic acid (MOPS), 4-(2-hydroxyethyl)-1-piperazineethanesulfonic acid (HEPES), a phosphate buffer, acetic acid, ascorbic acid, sulfosalicylic acid, formic acid, glycine, glycine-glycine, malic acid, or succinic acid.

In some embodiments the two different buffers are selected from citric acid, tris(2-carboxyethyl)phosphine hydrochloride (TCEP-HCl), oxidized form of tris(2-carboxyethyl)phosphine hydrochloride (TCEPO-HCl), 2-amino-2-hydroxymethyl-propane-1,3-diol (Tris), 2-(N-morpholino)ethanesulfonic acid (MES), 3-(N-morpholino)propanesulfonic acid (MOPS), 4-(2-hydroxyethyl)-1-piperazineethanesulfonic acid (HEPES), a phosphate buffer, acetic acid, ascorbic acid, sulfosalicylic acid, formic acid, glycine, glycine-glycine, malic acid and succinic acid.

In some embodiments the two different buffers are tris(2-carboxyethyl)phosphine hydrochloride (TCEP-HCl) and 3-(N-morpholino)propanesulfonic acid (MOPS); 2-(N-morpholino)ethanesulfonic acid (MES) and tris(2-carboxyethyl) phosphine hydrochloride (TCEP-HCl); or citric acid and 3-(N-morpholino)propanesulfonic acid (MOPS).

In some embodiments the two different buffers are tris(2-carboxyethyl)phosphine hydrochloride (TCEP-HCl) and 3-(N-morpholino)propanesulfonic acid (MOPS). In some embodiments the two different buffers are 2-(N-morpholino)ethanesulfonic acid (MES) and tris(2-carboxyethyl)phosphine hydrochloride (TCEP-HCl). In some embodiments the two different buffers are citric acid and 3-(N-morpholino)propanesulfonic acid (MOPS).

In some embodiments the two different buffers have the same concentration (a non-limiting example is. buffer (A) has a concentration of 88 mM and buffer (B) has a concentration of 88 mM). In some embodiments the two different buffers have different concentrations (a non-limiting example is buffer (A) has a concentration of 88 mM and buffer (B) has a concentration of 35 mM).

In some embodiments, the buffer is citric acid, tris(2-carboxyethyl)phosphine hydrochloride (TCEP-HCl), 3-(N-morpholino)propanesulfonic acid (MOPS), acetic acid, ascorbic acid, sulfosalicylic acid, formic acid, glycine, glycine-glycine, malic acid, or succinic acid, or any combination thereof.

In some embodiments, the buffer is citric acid, tris(2-carboxyethyl)phosphine hydrochloride (TCEP-HCl), 3-(N-morpholino)propanesulfonic acid (MOPS), acetic acid, ascorbic acid, sulfosalicylic acid, formic acid, glycine, glycine-glycine, malic acid, or succinic acid.

In some embodiments, the buffer is citric acid, tris(2-carboxyethyl)phosphine hydrochloride (TCEP-HCl), acetic acid, ascorbic acid, sulfosalicylic acid, formic acid, glycine, glycine-glycine, malic acid, or succinic acid, or any combination thereof.

In some embodiments, the buffer is citric acid, tris(2-carboxyethyl)phosphine hydrochloride (TCEP-HCl), 3-(N-morpholino)propanesulfonic acid (MOPS), or a combination thereof.

In some embodiments, the buffer is citric acid, tris(2-carboxyethyl)phosphine hydrochloride (TCEP-HCl), glycine-glycine, malic acid, or succinic acid.

In some embodiments, the buffer is citric acid, tris(2-carboxyethyl)phosphine hydrochloride (TCEP-HCl), malic acid, or succinic acid.

In some embodiments, the buffer is citric acid or tris(2-carboxyethyl)phosphine hydrochloride (TCEP-HCl).

In some embodiments, the buffer is citric acid. In some embodiments, the buffer is tris(2-carboxyethyl)phosphine hydrochloride (TCEP-HCl). In some embodiments the buffer is oxidized form of tris(2-carboxyethyl)phosphine hydrochloride (TCEPO-HCl). In some embodiments the buffer is 2-(N-morpholino)ethanesulfonic acid (MES). In some embodiments the buffer is 3-(N-morpholino)propanesulfonic acid (MOPS). In some embodiments the buffer is 2-amino-2-hydroxymethyl-propane-1,3-diol (Tris). In some embodiments the buffer is 4-(2-hydroxyethyl)-1-piperazineethanesulfonic acid (HEPES). In some embodiments the buffer is tartaric acid. In some embodiments the buffer is a phosphate buffer. In some embodiments the buffer is acetic acid. In some embodiments the buffer is ascorbic acid. In some embodiments the buffer is sulfosalicylic acid. In some embodiments the buffer is formic acid. In some embodiments the buffer is glycine. In some embodiments the buffer is glycine-glycine (Gly-Gly). In some embodiments the buffer is malic acid. In some embodiments the buffer is succinic acid.

In some embodiments, the buffer is in a dry state or a substantially dry state. In some embodiments the buffer is in a dry state. In some embodiments the buffer is in a substantially dry state.

The present invention is not limited to any specific concentration of the buffer. In various embodiments, the concentration of the buffer suitable for use with the present invention (e.g., compositions, methods, kits, solid matrices, matrix materials, formulations, etc.) is 1 mM-2M.

In various embodiments, the buffer has a concentration of 1 mM-2 M.

In various embodiments, the buffer has a concentration of 1 mM-10 mM, 1 mM-20 mM, 1 mM-30 mM, 1 mM-40 mM, 1 mM-50 mM, 1 mM-60 mM, 1 mM-70 mM, 1 mM-80 mM, 1 mM-90 mM, 1 mM-100 mM, 1 mM-110 mM, 1 mM-120 mM, 1 mM-130 mM, 1 mM-140 mM, 1 mM-150 mM, 1 mM-160 mM, 1 mM-170 mM, 1 mM-180 mM, 1 mM-190 mM, 1 mM-200 mM, 1 mM-210 mM, 1 mM-220 mM, 1 mM-230 mM, 1 mM-240 mM, 1 mM-250 mM, 1 mM-260 mM, 1 mM-270 mM, 1 mM-280 mM, 1 mM-290 mM, 1 mM-300 mM, 1 mM-310 mM, 1 mM-320 mM, 1 mM-330 mM, 1 mM-340 mM, 1 mM-350 mM, 1 mM-360 mM, 1 mM-370 mM, 1 mM-380 mM, 1 mM-390 mM, 1 mM-400 mM, 1 mM-410 mM, 1 mM-420 mM, 1 mM-430 mM, 1 mM-440 mM, 1 mM-450 mM, 1 mM-460 mM, 1 mM-470 mM, 1 mM-480 mM, 1 mM-490 mM, 1 mM-500 mM, 1 mM-600 mM, 1 mM-650 mM, 1 mM-700 mM, 1 mM-750 mM, 1 mM-800 mM, 1 mM-850 mM, 1 mM-900 mM, 1 mM-950 mM, 1 mM-1M, 1 mM-1.1 M, 1 mM-1.2 M, 1 mM-1.3 M, 1 mM-1.4 M, 1 mM-1.5 M, 1 mM-1.6 M, 1 mM-1.7 M, 1 mM-1.8 M, 1 mM-1.9 M, or 1 mM-2 M.

In various embodiments, the buffer has a concentration of 10 mM-20 mM, 10 mM-30 mM, 10 mM-40 mM, 10 mM-50 mM, 10 mM-60 mM, 10 mM-70 mM, 10 mM-80 mM, 10 mM-90 mM, 10 mM-100 mM, 10 mM-110 mM, 10 mM-120 mM, 10 mM-130 mM, 10 mM-140 mM, 10 mM-150 mM, 10 mM-160 mM, 10 mM-170 mM, 10 mM-180 mM, 10 mM-190 mM, 10 mM-200 mM, 10 mM-210 mM, 10 mM-220 mM, 10 mM-230 mM, 10 mM-240 mM, 10 mM-250 mM, 10 mM-260 mM, 10 mM-270 mM, 10 mM-280 mM, 10 mM-290 mM, 10 mM-300 mM, 10 mM-310 mM, 10 mM-320 mM, 10 mM-330 mM, 10 mM-340 mM, 10 mM-350 mM, 10 mM-360 mM, 10 mM-370 mM, 10 mM-380 mM, 10 mM-390 mM, 10 mM-400 mM, 10 mM-410 mM, 10 mM-420 mM, 10 mM-430 mM, 10 mM-440 mM, 10 mM-450 mM, 10 mM-460 mM, 10 mM-470 mM, 10 mM-480 mM, 10 mM-490 mM, 10 mM-500 mM, 10 mM-600 mM, 10 mM-650 mM, 10 mM-700 mM, 10 mM-750 mM, 10 mM-800 mM, 10 mM-850 mM, 10 mM-900 mM, 10 mM-950 mM, 10 mM-1M, 10 mM-1.1 M, 10 mM-1.2 M, 10 mM-1.3 M, 10 mM-1.4 M, 10 mM-1.5 M, 10 mM-1.6 M, 10 mM-1.7 M, 10 mM-1.8 M, 10 mM-1.9 M, or 10 mM-2 M.

In various embodiments, the buffer has a concentration of 20 mM-30 mM, 20 mM-40 mM, 20 mM-50 mM, 20 mM-60 mM, 20 mM-70 mM, 20 mM-80 mM, 20 mM-90 mM, 20 mM-100 mM, 20 mM-110 mM, 20 mM-120 mM, 20 mM-130 mM, 20 mM-140 mM, 20 mM-150 mM, 20 mM-160 mM, 20 mM-170 mM, 20 mM-180 mM, 20 mM-190 mM, 20 mM-200 mM, 20 mM-210 mM, 20 mM-220 mM, 20 mM-230 mM, 20 mM-240 mM, 20 mM-250 mM, 20 mM-260 mM, 20 mM-270 mM, 20 mM-280 mM, 20 mM-290 mM, 20 mM-300 mM, 20 mM-310 mM, 20 mM-320 mM, 20 mM-330 mM, 20 mM-340 mM, 20 mM-350 mM, 20 mM-360 mM, 20 mM-370 mM, 20 mM-380 mM, 20 mM-390 mM, 20 mM-400 mM, 20 mM-410 mM, 20 mM-420 mM, 20 mM-430 mM, 20 mM-440 mM, 20 mM-450 mM, 20 mM-460 mM, 20 mM-470 mM, 20 mM-480 mM, 20 mM-490 mM, 20 mM-500 mM, 20 mM-600 mM, 20 mM-650 mM, 20 mM-700 mM, 20 mM-750 mM, 20 mM-800 mM, 20 mM-850 mM, 20 mM-900 mM, 20 mM-950 mM, 20 mM-1M, 20 mM-1.1 M, 20 mM-1.2 M, 20 mM-1.3 M, 20 mM-1.4 M, 20 mM-1.5 M, 20 mM-1.6 M, 20 mM-1.7 M, 20 mM-1.8 M, 20 mM-1.9 M, or 20 mM-2 M.

In various embodiments, the concentration of the buffer is 1 mM-1.5 M. In various embodiments, the concentration of the buffer is 1 mM-1 M. In various embodiments, the concentration of the buffer is 1 mM-500 mM. In various embodiments, the concentration of the buffer is 1 mM-300 mM. In various embodiments, the concentration of the buffer is 1 mM-200 mM. In various embodiments, the concentration of the buffer is 1 mM-180 mM. In various embodiments, the concentration of the buffer is 1 mM-150 mM.

In various embodiments, the concentration of the buffer is 10 mM-1.5 M. In various embodiments, the concentration of the buffer is 10 mM-1 M. In various embodiments, the concentration of the buffer is 10 mM-500 mM. In various embodiments, the concentration of the buffer is 10 mM-300 mM. In various embodiments, the concentration of the buffer is 10 mM-200 mM. In various embodiments, the concentration of the buffer is 10 mM-180 mM. In various embodiments, the concentration of the buffer is 10 mM-150 mM.

In various embodiments, the concentration of the buffer is 20 mM-1.5 M. In various embodiments, the concentration of the buffer is 20 mM-1 M. In various embodiments, the concentration of the buffer is 20 mM-500 mM. In various embodiments, the concentration of the buffer is 20 mM-300 mM. In various embodiments, the concentration of the buffer is 20 mM-200 mM. In various embodiments, the concentration of the buffer is 20 mM-180 mM. In various embodiments, the concentration of the buffer is 20 mM-150 mM.

In various embodiments, the concentration of the buffer is 35 mM to 150 mM. In some embodiments, the concentration of the buffer is 35 mM. In some embodiments, the concentration of the buffer is 40 mM. In some embodiments, the concentration of the buffer is 88 mM. In some embodiments, the concentration of the buffer is 100 mM. In some embodiments, the concentration of the buffer is 150 mM.

The skilled artisan would recognize that the pH of the buffer selected for use in the various embodiments of the compositions and methods of the present invention is relevant. The pH of the buffer will typically be in the range of 2.0 to 8.0, 2.0 to 7.9, 2.0 to 7.8, 2.0 to 7.7, 2.0 to 7.6, 2.0 to 7.5, 2.0 to 7.4, 2.0 to 7.3, 2.0 to 7.2, 2.0 to 7.1, 2.0 to 7.0, 2.0 to 6.9, 2.0 to 6.8, 2.0 to 6.7, 2.0 to 6.6, 2.0 to 6.5, 2.0 to 6.4, 2.0 to 6.3, 2.0 to 6.2, 2.0 to 6.1, 2.0 to 6.0, 2.0 to 5.9, 2.0 to 5.8, 2.0 to 5.7, 2.0 to 5.6; 2.0 to 5.5, 2.0 to 5.4, 2.0 to 5.3, 2.0 to 5.2, 2.0 to 5.1, 2.0 to 5.0, 2.0 to 4.9, 2.0 to 4.8, 2.0 to 4.7, 2.0 to 4.6, 2.0 to 4.5, 2.0 to 4.4, 2.0 to 4.3, 2.0 to 4.2, 2.0 to 4.1, 2.0 to 4.0, 2.0 to 3.9, 2.0 to 3.8, 2.0 to 3.7, 2.0 to 3.6, 2.0 to 3.5, 2.0 to 3.4, 2.0 to 3.3, 2.0 to 3.2, 2.0 to 3.1, 2.0 to 3.0, 3.0 to 8.0, 3.0 to 7.9, 3.0 to 7.8, 3.0 to 7.7, 3.0 to 7.6, 3.0 to 7.5, 3.0 to 7.4, 3.0 to 7.3, 3.0 to 7.2, 3.0 to 7.1, 3.0 to 7.0, 3.0 to 6.9, 3.0 to 6.8, 3.0 to 6.7, 3.0 to 6.6, 3.0 to 6.5, 3.0 to 6.4, 3.0 to 6.3, 3.0 to 6.2, 3.0 to 6.1, 3.0 to 6.0, 3.0 to 5.9, 3.0 to 5.8, 3.0 to 5.7, 3.0 to 5.6; 3.0 to 5.5, 3.0 to 5.4, 3.0 to 5.3, 3.0 to 5.2, 3.0 to 5.1, 3.0 to 5.0, 3.0 to 4.9, 3.0 to 4.8, 3.0 to 4.7, 3.0 to 4.6, 3.0 to 4.5, 3.0 to 4.4, 3.0 to 4.3, 3.0 to 4.2, 3.0 to 4.1, 3.0 to 4.0, 4.0 to 8.0, 4.0 to 7.9, 4.0 to 7.8, 4.0 to 7.7, 4.0 to 7.6, 4.0 to 7.5, 4.0 to 7.4, 4.0 to 7.3, 4.0 to 7.2, 4.0 to 7.1, 4.0 to 7.0, 4.0 to 6.9, 4.0 to 6.8, 4.0 to 6.7, 4.0 to 6.6, 4.0 to 6.5, 4.0 to 6.4, 4.0 to 6.3, 4.0 to 6.2, 4.0 to 6.1, 4.0 to 6.0, 4.0 to 5.9, 4.0 to 5.8, 4.0 to 5.7, 4.0 to 5.6; 4.0 to 5.5, 4.0 to 5.4, 4.0 to 5.3, 4.0 to 5.2, 4.0 to 5.1, 4.0 to 5.0, 5.0 to 8.0, 5.0 to 7.9, 5.0 to 7.8, 5.0 to 7.7, 5.0 to 7.6, 5.0 to 7.5, 5.0 to 7.4, 5.0 to 7.3, 5.0 to 7.2, 5.0 to 7.1, 5.0 to 7.0, 5.0 to 6.9, 5.0 to 6.8, 5.0 to 6.7, 5.0 to 6.6, 5.0 to 6.5, 5.0 to 6.4, 5.0 to 6.3, 5.0 to 6.2, 5.0 to 6.1, 5.0 to 6.0, 6.0 to 8.0, 6.0 to 7.9, 6.0 to 7.8, 6.0 to 7.7, 6.0 to 7.6, 6.0 to 7.5, 6.0 to 7.4, 6.0 to 7.3, 6.0 to 7.2, 6.0 to 7.1, 6.0 to 7.0, 7.0 to 8.0, 3.5 to 4.5, 3.5 to 7.0, or 4.5 to 7.0. In some embodiments the pH of the buffer is 3.5. In some embodiments the pH of the buffer is 4.5. In some embodiments the pH of the buffer is 7.0. In some embodiments, the buffer has a pH of 3.0 to 8.0. In some embodiments, the buffer has a pH of 2.0 to 8.0. In some embodiments, the buffer has a pH of 3.5 to 4.5. In some embodiments, the buffer has a pH of 3.0 to 5.0. In some embodiments, the buffer has a pH of 3.5 to 7.0.

In some embodiments, the buffer does not contain or comprise or consist essentially of or consist of a denaturant. In some embodiments, the buffer does not contain or comprise or consist essentially of or consist of a protein denaturant. In some embodiments, the buffer does not contain or comprise or consist essentially of or consist of a denaturant, a protein denaturant, a reducing agent, an antioxidant, a UV protectant, a free-radical scavenger, a chelator, an RNase inhibitor or any combination thereof. In some embodiments, the buffer does not contain or comprise or consist essentially of or consist of a denaturant, a protein denaturant, a reducing agent, an antioxidant, a UV protectant, a free-radical scavenger, a chelator, and/or an RNase inhibitor. In some embodiments the buffer does not comprise a denaturant. In some embodiments the buffer does not comprise a protein denaturant.

The skilled artisan would recognize that the pH of the compositions and/or formulations selected for use in the various embodiments of the compositions and methods of the present invention is relevant. The pH of the compositions and/or formulations will typically be in the range of 2.0 to 8.0, 2.0 to 7.9, 2.0 to 7.8, 2.0 to 7.7, 2.0 to 7.6, 2.0 to 7.5, 2.0 to 7.4, 2.0 to 7.3, 2.0 to 7.2, 2.0 to 7.1, 2.0 to 7.0, 2.0 to 6.9, 2.0 to 6.8, 2.0 to 6.7, 2.0 to 6.6, 2.0 to 6.5, 2.0 to 6.4, 2.0 to 6.3, 2.0 to 6.2, 2.0 to 6.1, 2.0 to 6.0, 2.0 to 5.9, 2.0 to 5.8, 2.0 to 5.7, 2.0 to 5.6; 2.0 to 5.5, 2.0 to 5.4, 2.0 to 5.3, 2.0 to 5.2, 2.0 to 5.1, 2.0 to 5.0, 2.0 to 4.9, 2.0 to 4.8, 2.0 to 4.7, 2.0 to 4.6, 2.0 to 4.5, 2.0 to 4.4, 2.0 to 4.3, 2.0 to 4.2, 2.0 to 4.1, 2.0 to 4.0, 2.0 to 3.9, 2.0 to 3.8, 2.0 to 3.7, 2.0 to 3.6, 2.0 to 3.5, 2.0 to 3.4, 2.0 to 3.3, 2.0 to 3.2, 2.0 to 3.1, 2.0 to 3.0, 3.0 to 8.0, 3.0 to 7.9, 3.0 to 7.8, 3.0 to 7.7, 3.0 to 7.6, 3.0 to 7.5, 3.0 to 7.4, 3.0 to 7.3, 3.0 to 7.2, 3.0 to 7.1, 3.0 to 7.0, 3.0 to 6.9, 3.0 to 6.8, 3.0 to 6.7, 3.0 to 6.6, 3.0 to 6.5, 3.0 to 6.4, 3.0 to 6.3, 3.0 to 6.2, 3.0 to 6.1, 3.0 to 6.0, 3.0 to 5.9, 3.0 to 5.8, 3.0 to 5.7, 3.0 to 5.6; 3.0 to 5.5, 3.0 to 5.4, 3.0 to 5.3, 3.0 to 5.2, 3.0 to 5.1, 3.0 to 5.0, 3.0 to 4.9, 3.0 to 4.8, 3.0 to 4.7, 3.0 to 4.6, 3.0 to 4.5, 3.0 to 4.4, 3.0 to 4.3, 3.0 to 4.2, 3.0 to 4.1, 3.0 to 4.0, 4.0 to 8.0, 4.0 to 7.9, 4.0 to 7.8, 4.0 to 7.7, 4.0 to 7.6, 4.0 to 7.5, 4.0 to 7.4, 4.0 to 7.3, 4.0 to 7.2, 4.0 to 7.1, 4.0 to 7.0, 4.0 to 6.9, 4.0 to 6.8, 4.0 to 6.7, 4.0 to 6.6, 4.0 to 6.5, 4.0 to 6.4, 4.0 to 6.3, 4.0 to 6.2, 4.0 to 6.1, 4.0 to 6.0, 4.0 to 5.9, 4.0 to 5.8, 4.0 to 5.7, 4.0 to 5.6; 4.0 to 5.5, 4.0 to 5.4, 4.0 to 5.3, 4.0 to 5.2, 4.0 to 5.1, 4.0 to 5.0, 5.0 to 8.0, 5.0 to 7.9, 5.0 to 7.8, 5.0 to 7.7, 5.0 to 7.6, 5.0 to 7.5, 5.0 to 7.4, 5.0 to 7.3, 5.0 to 7.2, 5.0 to 7.1, 5.0 to 7.0, 5.0 to 6.9, 5.0 to 6.8, 5.0 to 6.7, 5.0 to 6.6, 5.0 to 6.5, 5.0 to 6.4, 5.0 to 6.3, 5.0 to 6.2, 5.0 to 6.1, 5.0 to 6.0, 6.0 to 8.0, 6.0 to 7.9, 6.0 to 7.8, 6.0 to 7.7, 6.0 to 7.6, 6.0 to 7.5, 6.0 to 7.4, 6.0 to 7.3, 6.0 to 7.2, 6.0 to 7.1, 6.0 to 7.0, 7.0 to 8.0, 3.5 to 4.5, 3.5 to 7.0, or 4.5 to 7.0. In some embodiments the pH of the compositions and/or formulations is 3.5. In some embodiments the pH of the compositions and/or formulations is 4.5. In some embodiments the pH of the compositions and/or formulations is 7.0. In some embodiments, the compositions and/or formulations has a pH of 3.0 to 8.0. In some embodiments, the buffer has a pH of 2.0 to 8.0. In some embodiments, the compositions and/or formulations has a pH of 3.5 to 4.5. In some embodiments, the compositions and/or formulations has a pH of 3.0 to 5.0. In some embodiments, the compositions and/or formulations has a pH of 3.5 to 7.0.

The terms "UV protectant" or "radical trap" or "antioxidant" may be used interchangeably herein. Non-limiting examples of antioxidants include hydroquinone monomethyl ether (MEHQ), hydroquinone (HQ), and toluhydroquinone (THQ). Moreover, any combination of these or other antioxidants known in the art may be used to practice the invention. In some embodiments the anitioxidant is one or more of hydroquinone monomethyl ether (MEHQ), hydroquinone (HQ), and/or toluhydroquinone (THQ). In some embodiments the anitioxidant is hydroquinone monomethyl ether (MEHQ), hydroquinone (HQ), or toluhydroquinone (THQ). In some embodiments the antioxidant is hydroquinone (HQ). In some embodiments the antioxidant is toluhydroquinone (THQ). In some embodiments, the antioxidant is hydroquinone monomethyl ether (MEHQ).

The present invention is not limited to any specific concentration of the antioxidant. In various embodiments, the concentration of the antioxidant suitable for use with the present invention (e.g., compositions, methods, kits, solid matrices, matrix materials, formulations, etc.) is 1 mM-200 mM.

In various embodiments, the antioxidant has a concentration of 1 mM-200 mM. In various embodiments, the antioxidant has a concentration of 1 mM-200 mM, 1 mM-175 mM, 1 mM-150 mM, 1 mM-125 mM, 1 mM-100 mM, 1 mM-75 mM, 1 mM-50 mM, 1 mM-25 mM, 1 mM-10 mM, 10 mM-200 mM, 10 mM-175 mM, 10 mM-150 mM, 10 mM-125 mM, 10 mM-100 mM, 10 mM-75 mM, 10 mM-50 mM, 10 mM-25 mM, 20 mM-200 mM, 20 mM-175 mM, 20 mM-150 mM, 20 mM-125 mM, 20 mM-100 mM, 20 mM-75 mM, or 20 mM-50 mM.

In various embodiments, the concentration of the antioxidant is 1 mM to 150 mM. In various embodiments, the concentration of the antioxidant is 1 mM to 100 mM. In various embodiments, the concentration of the antioxidant is 1 mM to 80 mM. In various embodiments, the concentration of the antioxidant is 1 mM to 60 mM.

In various embodiments, the concentration of the antioxidant is 10 mM to 150 mM. In various embodiments, the concentration of the antioxidant is 10 mM to 100 mM. In various embodiments, the concentration of the antioxidant is 10 mM to 80 mM. In various embodiments, the concentration of the antioxidant is 10 mM to 60 mM.

In various embodiments, the concentration of the antioxidant is 20 mM to 150 mM. In various embodiments, the concentration of the antioxidant is 20 mM to 100 mM. In various embodiments, the concentration of the antioxidant is 20 mM to 80 mM. In various embodiments, the concentration of the antioxidant is 20 mM to 60 mM. In some embodiments, the concentration of the antioxidant is 40 mM.

The term "denaturant" as used herein is any substance that causes denaturation of proteins and/or other biological compounds. The skilled artisan will appreciate that numerous denaturants are known in the art and can be empirically selected for use in the compositions and methods described herein. Non-limiting examples of denaturants include guanidinium thiocyanate, guanidinium hydrochloride, arginine, sodium dodecyl sulfate (SDS), sodium thiocyanate, urea, and thiourea. Moreover, any combination of these or other denaturants known in the art may be used to practice the invention. In some embodiments the denaturant is one or more of guanidinium thiocyanate, guanidinium hydrochloride, arginine, sodium dodecyl sulfate (SDS), sodium thiocyanate, urea, and/or thiourea. In some embodiments the denaturant is guanidinium thiocyanate, guanidinium hydrochloride, arginine, sodium dodecyl sulfate (SDS), sodium thiocyanate, urea, or thiourea. In some embodiments the denaturant is guanidinium thiocyanate, guanidinium hydrochloride, arginine, sodium dodecyl sulfate (SDS), sodium thiocyanate, urea, or thiourea.

In some embodiments, the denaturant is sodium thiocyanate. In some embodiments, the denaturant is urea. In some embodiments, the denaturant is thiourea. In some embodiments the denaturant is guanidinium thiocyanate. In some embodiments the denaturant is guanidinium hydrochloride. In some embodiments the denaturant is arginine. In some embodiments the denaturant is sodium dodecyl sulfate (SDS).

In some embodiments, the denaturant is a protein denaturant.

In various embodiments, a denaturant is not present in the present invention for example, in other words, a denaturant is not present in the compositions, methods, kits, solid matrices, matrix materials, etc. of the present invention.

In various embodiments, the concentration of the denaturant suitable for use with the present invention (e.g., compositions, methods, kits, solid matrices, matrix materials, formulations, etc.) is 10 mM-12 M.

In various embodiments, the denaturant has a concentration of 10 mM-12 M. In various embodiments, the denaturant has a concentration of 10 mM-12 M, 10 mM-11 M, 10 mM-10 M, 10 mM-9 M, 10 mM-8 M, 10 mM-7 M, 10 mM-6 M, 10 mM-5 M, 10 mM-4 M, 10 mM-3 M, 10 mM-2 M, 10 mM-1 M, 10 mM-900 mM, 10 mM-800 mM, 10 mM-700 mM, 10 mM-600 mM, 10 mM-500 mM, 10 mM-400 mM, or 10 mM-300 mM. In some embodiments, the denaturant has a concentration of 420 mM.

The terms "solid matrix" and "stabilized solid matrix" are used interchangeably herein. As used herein, the term "solid matrix" and "stabilized solid matrix" includes without limitation any matrix material that has been contacted with or treated with a composition of the invention and/or embodiment thereof (i.e. a composition for stabilizing a biological sample and/or nucleic acid on a matrix material) and/or formulation of the invention and/or buffer. This also includes any matrix material to which a composition of the invention or embodiment thereof (i.e. a composition for stabilizing a biological sample and/or nucleic acid on a matrix material) and/or formulation of the invention and/or buffer has been applied to.

In some embodiments, the term "solid matrix" or "stabilized solid matrix" refers to a matrix material and a composition of the invention or a formulation of the invention, wherein the composition of the invention or the formulation of the invention is impregnated in or incorporated in or entrained in the matrix material in a dry state or substantially dry state.

In some embodiments, the term "solid matrix" or "stabilized solid matrix" refers to a matrix material and a buffer, wherein the buffer is impregnated in or incorporated into or entrained in the matrix material. In some embodiments, the buffer is impregnated in or incorporated into or entrained in the matrix material in a dry state or substantially dry state. In some embodiments, the solid matrix consists essentially of a matrix material and a buffer. In some embodiments, the solid matrix consists essentially of a matrix material and a buffer, wherein the buffer is impregnated or incorporated in or entrained in the matrix material in a dry state or substantially dry state. In some embodiments, the solid matrix consists essentially of a matrix material and a buffer, wherein the buffer is impregnated or incorporated in or entrained in the matrix material in a dry state or substantially dry state and the matrix material is in a dry state or substantially dry state.

In some embodiments, the solid matrix consists of a matrix material and a buffer. In some embodiments, the solid matrix consists of a matrix material and a buffer, wherein the buffer is impregnated or incorporated in or entrained in the matrix material in a dry state or substantially dry state. In some embodiments, the solid matrix consists of a matrix material and a buffer, wherein the buffer is impregnated or incorporated in or entrained in the matrix material in a dry state or substantially dry state and the matrix material is in a dry state or substantially dry state.

In some embodiments, the solid matrix comprises a matrix material and a buffer, wherein the solid matrix does not comprise a denaturant. In some embodiments, the solid matrix comprises a matrix material and a buffer, wherein the buffer is impregnated or incorporated in or entrained in the matrix material in a dry state or substantially dry state, wherein the solid matrix does not comprise a denaturant. In some embodiments, the solid matrix comprises a matrix material and a buffer, wherein the buffer is impregnated or incorporated in or entrained in the matrix material in a dry state or substantially dry state and the matrix material is in a dry state or substantially dry state, and wherein the solid matrix material does not comprise a denaturant.

In some embodiments, the solid matrix is in the form of a pellet or tablet. In some embodiments, the solid matrix is of a porous nature to provide impregnation or incorporation or entrainment of the biological sample into or onto the solid matrix. As used herein, the term "entrain" means that during storage the biological sample and/or nucleic acids is bound to the solid matrix without substantial reliance on ionic, covalent, or van der Waals interactions.

In some embodiments, the solid matrix is contacted with a biological sample (or a biological sample is sorbed onto the solid matrix) such that the solid matrix does not inhibit storage, stabilization, preservation, recovery or subsequent analysis of the biological sample or contents of the biological sample (e.g., nucleic acids).

The terms "solid matrix" and "stabilized solid matrix" are used interchangeably herein. In some embodiments, the solid matrix is in a dry state or a substantially dry state. In some embodiments the solid matrix is in a dry state. In some embodiments the solid matrix is in a substantially dry state. In some embodiments, the solid matrix, the matrix material and the buffer are each independently in a dry state or substantially dry state.

In some embodiments, the solid matrix does not contain or comprise or consist essentially of or consist of a denaturant. In some embodiments, the solid matrix does not contain or comprise or consist essentially of or consist of a protein denaturant. In some embodiments, the solid matrix does not contain or comprise or consist essentially of or consist of a denaturant, a protein denaturant, a reducing agent, an antioxidant, a UV protectant, a free-radical scavenger, a chelator, an RNase inhibitor or any combination thereof. In some embodiments, the solid matrix does not contain or comprise or consist essentially of or consist of a denaturant, a protein denaturant, a reducing agent, an antioxidant, a UV protectant, a free-radical scavenger, a chelator, and/or an RNase inhibitor. In some embodiments the solid matrix does not comprise a denaturant. In some embodiments the solid matrix does not comprise a protein denaturant.

In some embodiments, the solid matrix comprises a matrix material, at least one buffer, at least one optional denaturant, at least one optional reducing agent; and at least one optional antioxidant, wherein the buffer, optional denaturant, optional reducing agent, and optional antioxidant are each impregnated in or incorporated in or entrained in the matrix material in a substantially dry state or dry state.

In some embodiments, the solid matrix comprises a matrix material, at least one buffer, at least one optional reducing agent; and at least one optional antioxidant wherein the buffer, optional denaturant, optional reducing agent, and optional antioxidant are each impregnated in or incorporated in or entrained in the matrix material in a substantially dry state or dry state, provided that the solid matrix does not comprise a denaturant.

The term "matrix material" refers without limitation to any material to which the composition and/or formulation of the invention and/or buffer and/or the biological sample and/or nucleic acid will sorb and which does not inhibit storage or subsequent analysis of the biological sample or contents of the biological sample (e.g., nucleic acids). This includes flat dry matrices or a matrix combined with a binder to form a pellet or tablet to which the composition and/or formulation of the invention and/or buffer and/or the biological sample and/or nucleic acid is sorbed. In some embodiments, the matrix material is of a porous nature to provide entrainment of the composition and/or formulation of the invention and/or buffer and/or the biological sample and/or nucleic acid into or onto the matrix material. As used herein, the term "entrain" means that during storage the composition and/or formulation of the invention and/or buffer and/or the biological sample and/or nucleic acid is bound to the matrix material without substantial reliance on ionic, covalent, or van der Waals interactions.

In various embodiments the matrix material is a non-dissolvable substantially dry solid material or a non-dissolvable dry solid material. In various embodiments, the matrix material is a non-dissolvable dry solid material. In various embodiments, the matrix material is a non-dissolvable substantially dry solid material. Non-limiting examples of matrix materials include cellulose based materials (e.g., cellulose, nitrocellulose, or carboxymethylcellulose papers), hydrophilic polymers including synthetic hydrophilic polymers (e.g., polyester, polyamide, carbohydrate polymers), polytetrafluoroethylene (Empore™, 3M, St. Paul, Minn.), fiberglass, carbon fiber, and porous ceramics. Additional non-limiting examples of matrix materials include cellulose-based products, cellulosic paper, cellulose paper, cellulose, cellulose acetate, glass fibers, or any combination thereof. In some embodiments, the matrix material may be porous. In some embodiments, the matrix material is cellulose paper. In some embodiments, the matrix material is a porous cellulose paper. Non-limiting examples of porous cellulose paper include Whatman™ 903, and PerkinElmer™ 226. Non-limiting examples of porous cellulosic paper include Whatman™ 903, and PerkinElmer™ 226. Non-limiting examples of porous cellulose paper include Whatman™ 903, PerkinElmer™ 226, 31-ETF, FTA™, or FTA™ Elute. In some embodiments, the matrix material is cellulosic paper. In some embodiments, the matrix material is in the form of a pellet or tablet. In some embodiments, the matrix material is in a dry state or a substantially dry state.

In some embodiments the matrix material is a cellulose based material (e.g., cellulose, nitrocellulose, or carboxymethylcellulose papers), hydrophilic polymers including synthetic hydrophilic polymers (e.g., polyester, polyamide, carbohydrate polymers), polytetrafluoroethylene fiberglass, carbon fiber, porous ceramics cellulose-based products, cellulosic paper, filter paper, cellulose paper, cellulose, cellulose acetate, or glass fibers, or combinations thereof.

In some embodiments the matrix material is a cellulose based material (e.g., cellulose, nitrocellulose, or carboxymethylcellulose papers). In some embodiments the matrix material is hydrophilic polymers including synthetic hydrophilic polymers (e.g., polyester, polyamide, carbohydrate polymers). In some embodiments the matrix material is polytetrafluoroethylene fiberglass. In some embodiments the matrix material is carbon fiber. In some embodiments the matrix material is porous ceramics cellulose-based products. In some embodiments the matrix material is filter paper. In some embodiments the matrix material is cellulose paper. In some embodiments the matrix material is cellulose. In some embodiments the matrix material is cellulose acetate. In some embodiments the matrix material is glass fibers. In some embodiments the matrix material is cellulosic paper.

In some embodiments, the matrix material is in a dry state or a substantially dry state. In some embodiments the matrix material is in a substantially dry state. In some embodiments the matrix material is in a dry state.

In some embodiments, the non-dissolvable dry solid material is a cellulose based material (e.g., cellulose, nitrocellulose, or carboxymethylcellulose papers), hydrophilic polymers including synthetic hydrophilic polymers (e.g., polyester, polyamide, carbohydrate polymers), polytetrafluoroethylene fiberglass, carbon fiber, porous ceramics, cellulose-based products, cellulosic paper, cellulose paper, filter paper, cellulose, cellulose acetate, or glass fibers, or combinations thereof.

In some embodiments the non-dissolvable dry solid material is a cellulose based material (e.g., cellulose, nitrocellulose, or carboxymethylcellulose papers). In some embodiments the non-dissolvable dry solid material is hydrophilic polymers including synthetic hydrophilic polymers (e.g., polyester, polyamide, carbohydrate polymers). In some embodiments the non-dissolvable dry solid material is polytetrafluoroethylene fiberglass. In some embodiments the non-dissolvable dry solid material is carbon fiber. In some embodiments the non-dissolvable dry solid material is porous ceramics. In some embodiments the non-dissolvable dry solid material is cellulose-based product. In some embodiments the non-dissolvable dry solid material is cellulose paper. In some embodiments the non-dissolvable dry solid material is filter paper. In some embodiments the non-dissolvable dry solid material is cellulose. In some embodiments the non-dissolvable dry solid material is cellulose acetate. In some embodiments the non-dissolvable dry solid material is glass fibers. In some embodiments, the non-dissolvable dry solid material is cellulosic paper.

In some embodiments the non-dissolvable substantially dry solid material is a cellulose based material (e.g., cellulose, nitrocellulose, or carboxymethylcellulose papers), hydrophilic polymers including synthetic hydrophilic polymers (e.g., polyester, polyamide, carbohydrate polymers), polytetrafluoroethylene fiberglass, carbon fiber, porous ceramics, cellulose-based products, cellulosic paper, filter paper, cellulose paper, cellulose, cellulose acetate, or glass fibers, or combinations thereof.

In some embodiments the non-dissolvable substantially dry solid material is a cellulose based material (e.g., cellulose, nitrocellulose, or carboxymethylcellulose papers). In some embodiments the non-dissolvable substantially dry solid material is hydrophilic polymers including synthetic hydrophilic polymers (e.g., polyester, polyamide, carbohydrate polymers). In some embodiments the non-dissolvable substantially dry solid material is polytetrafluoroethylene fiberglass. In some embodiments the non-dissolvable substantially dry solid material is carbon fiber. In some embodiments the non-dissolvable substantially dry solid material is porous ceramics. In some embodiments the non-dissolvable substantially dry solid material is cellulose-based product. In some embodiments the non-dissolvable substantially dry solid material is cellulose paper. In some embodiments the non-dissolvable substantially dry solid material is filter paper. In some embodiments the non-dissolvable substantially dry solid material is cellulose. In some embodiments the non-dissolvable substantially dry solid material is cellulose acetate. In some embodiments the non-dissolvable substantially dry solid material is glass fibers. In some embodiments the non-dissolvable substantially dry solid material is cellulosic paper.

In some embodiments, the matrix material does not contain or comprise or consist essentially of or consist of a denaturant. In some embodiments, the matrix material does not contain or comprise or consist essentially of or consist of a protein denaturant. In some embodiments, the matrix material does not contain or comprise or consist essentially of or consist of a denaturant, a protein denaturant, a reducing agent, an antioxidant, a UV protectant, a free-radical scavenger, a chelator, an RNase inhibitor or any combination thereof. In some embodiments, the matrix material does not contain or comprise or consist essentially of or consist of a denaturant, a protein denaturant, a reducing agent, an antioxidant, a UV protectant, a free-radical scavenger, a chelator, and/or an RNase inhibitor. In some embodiments the matrix material does not comprise a denaturant. In some embodiments the matrix material does not comprise a protein denaturant.

As used herein, the term "sorb" means that the composition of the invention and/or formulation of the invention and/or buffer and/or the biological sample and/or nucleic acid is absorbed, adsorbed or otherwise incorporated into or onto the matrix material and/or solid matrix in such a way as not to be readily removed from the matrix material and/or solid matrix unless subjected to conditions which are intentionally or inadvertently performed to remove the sorbed composition and/or buffer and/or biological sample and/or nucleic acid from the matrix material and/or solid matrix.

As used herein, the terms "analysis" or "analyzed" or "analyzing" or "subsequent analysis" includes without limitation any analysis which may be performed on a biological sample and/or nucleic acid stored on the solid matrix. The biological sample and/or nucleic acid stored on the solid matrix may be analyzed in vitro. The biological sample and/or nucleic acid may first be removed from the solid matrix prior to analysis. The nucleic acid may be subjected to chemical, biochemical, biological, or analytical analysis or a combination thereof. Non-limiting examples of analysis which may be performed on biological samples and/or nucleic acids stored and/or extracted onto and/or recovered from the solid matrix include polymerase chain reaction (PCR), ligase chain reaction (LCR), reverse transcriptase initiated PCR, DNA or RNA hybridization techniques including without limitation restriction fragment length polymorphism (RFLP) and other techniques using genetic or DNA or RNA probes, or genomic sequencing. Other non-limiting examples of analysis which may be performed on biological samples and/or nucleic acids stored on and/or extracted onto and/or recovered from the solid matrix include using the stored and/or extracted onto and/or recovered biological samples and/or nucleic acids as a template for subsequent analysis using PCR methods. Non-limiting examples of PCR methods includes PCR using DNA or RNA as a template. When RNA is analyzed, the RNA may serve as a template using reverse transcriptase initiated PCR. The DNA sequence produced from the RNA template may then serve as a template for further PCR amplification. In some embodiments, the analysis may comprise quantitative Reverse Transcription Polymerase Chain Reaction (qRT-PCR).

Without being bound by theory, in a real time PCR assay a positive reaction is detected by accumulation of a fluorescent signal. The Ct (cycle threshold) is defined as the number of cycles required for the fluorescent signal to cross the threshold (i.e., exceed the background level). Ct levels are inversely proportional to the amount of target nucleic acid in the sample (i.e., the lower the Ct level the greater the amount of target nucleic acid in the sample; the higher the Ct level the lesser the amount of target nucleic acid in the sample.)

As used herein the term "solvent" means a substance that dissolves a solute (e.g., a chemically distinct liquid, solid, or gas), resulting in a solution. Non-limiting examples of solvents include any non-polar, polar aprotic, and/or polar protic solvents or combinations thereof as commonly known in the art. In one embodiment, the solvent is water.

As used herein the term "substantially dry" or "substantially dry state" refers to drying the sample (e.g., biological sample) and/or matrix material and/or buffer and/or solid matrix, and/or nucleic acids and/or denaturant and/or antioxidant and/or reducing agent and/or any combination thereof to have approximately less than or equal to 10% of solvent content to 1% solvent content (e.g., less than or equal to 10% water content to 1% water content). In some embodiments, "substantially dry state" refers to drying the sample (e.g., biological sample) and/or matrix material and/or buffer and/or solid matrix and/or nucleic acids and/or denaturant and/or antioxidant and/or reducing agent, and/or any combination thereof to have 10% to 1% solvent content, 9% to 1% solvent content, 8% to 1% solvent content, 7% to 1% solvent content, 6% to 1% solvent content, 5% to 1% solvent content, 4% to 1% solvent content, 3% to 1% solvent content, or 2% to 1% solvent content. In some embodiments, the solvent is water. In some embodiments, "substantially dry state" refers to drying the sample (e.g., biological sample) and/or matrix material and/or buffer and/or solid matrix and/or nucleic acids and/or denaturant and/or antioxidant and/or reducing agent, and/or any combination thereof to have 10 wt % to 1 wt % solvent, 9 wt % to 1 wt % solvent, 8 wt % to 1 wt % solvent, 7 wt % to 1 wt % solvent, 6 wt % to 1 wt % solvent, 5 wt % to 1 wt % solvent, 4 wt % to 1 wt % solvent, 3 wt % to 1 wt % solvent, or 2 wt % to 1 wt % solvent. In some embodiments, the solvent is water.

As used herein the term "dry" or "dry state" refers to drying the sample (e.g., biological sample) and/or matrix material and/or buffer and/or solid matrix and/or nucleic acids and/or denaturant and/or antioxidant and/or reducing agent, and/or any combination thereof to have approximately less than 1% of solvent content to 0% solvent content (e.g., less than 1 water content to 0% water content). In some embodiments, "dry state" refers to drying the sample (e.g., biological sample) and/or matrix material and/or buffer and/or solid matrix and/or nucleic acids and/or denaturant and/or antioxidant and/or reducing agent, and/or any combination thereof to have 0.99% to 0% solvent content, 0.9% to 0% solvent content, 0.9% to 0.25% solvent content, 0.9% to 0.1% solvent content, 0.5% to 0% solvent content, 0.5% to 0.1% solvent content, 0.5% to 0.25% solvent content, 0.25% to 0% solvent content, or 0.25% to 0.1% solvent content. In some embodiments, the solvent is water. In some embodiments, "dry state" refers to drying the sample (e.g., biological sample) and/or matrix material and/or buffer and/or solid matrix and/or nucleic acids and/or denaturant and/or antioxidant and/or reducing agent, and/or any combination thereof to have 0.99 wt % to 0 wt % solvent, 0.9 wt % to 0 wt % solvent, 0.9 wt % to 0.25 wt % solvent, 0.9 wt % to 0.1 wt % solvent, 0.5 wt % to 0 wt % solvent, 0.5 wt % to 0.1 wt % solvent, 0.5 wt % to 0.25 wt % solvent, 0.25 wt % to 0 wt % solvent, or 0.25 wt % to 0.1 wt % solvent. In some embodiments, the solvent is water.

TABLE 1

Formulations

| Formulation Number | Component 1 | Component 2 | Component 3 | Component 4 | Solvent | pH |
|---|---|---|---|---|---|---|
| 1 | 420 mM Sodium thiocyanate | 88 mM MOPS | 35 mM TCEP-HCl | 40 mM MEHQ | Water | 4.5 |
| 2 | 420 mM Urea | 88 mM MOPS | 35 mM TCEP-HCl | 40 mM MEHQ | Water | 4.5 |
| 3 | 420 mM Sodium thiocyanate | 88 mM MES | 35 mM TCEP-HCl | 40 mM MEHQ | Water | 4.5 |
| 4 | 420 mM Urea | 88 mM MOPS | | | Water | 3.5 |
| 5 | 420 mM Thiourea | 88 mM MOPS | | | Water | 3.5 |
| 6 | | 88 mM MOPS | 35 mM TCEP-HCl | 40 mM MEHQ | Water | 4.5 |

TABLE 1-continued

Formulations

| Formulation Number | Component 1 | Component 2 | Component 3 | Component 4 | Solvent | pH |
|---|---|---|---|---|---|---|
| 7 | 420 mM Urea | 88 mM MOPS | 35 mM TCEP-HCl | | Water | 4.5 |
| 8 | 420 mM Urea | 88 mM MOPS | 35 mM TCEP-HCl | | Water | 7.0 |
| 9 | 420 mM Urea | | 35 mM TCEP-HCl | | Water | 4.5 |
| 10 | | 88 mM MOPS | 35 mM TCEP-HCl | | Water | 4.5 |
| 11 | | | 35 mM TCEP-HCl | | Water | 4.5 |
| 12 | | | 35 mM TCEP-HCl | | Water | 3.5 |
| 13 | 420 mM Urea | 88 mM MOPS | 35 mM TCEP-HCl | 40 mM Ascorbic acid | Water | 4.5 |
| 14 | | | 100 mM Citric acid | | Water | 3.5 |
| 15 | 420 mM Urea | 88 mM MOPS | 100 mM Citric acid | | Water | 3.5 |
| 16 | | | 150 mM Citric acid | | Water | 3.5 |
| 17 | | | 100 mM Acetic acid | | Water | 3.5 |
| 18 | | | 100 mM Ascorbic acid | | Water | 3.5 |
| 19 | | | 100 mM Sulfosalicylic acid | | Water | 3.5 |
| 20 | | | 100 mM Formic acid | | Water | 3.5 |
| 21 | | | 100 mM Glycine | | Water | 3.5 |
| 22 | | | 100 mM Gly-Gly | | Water | 3.5 |
| 23 | | | 100 mM Malic acid | | Water | 3.5 |
| 24 | | | 100 mM Succinic acid | | Water | 3.5 |

Various Non-Limiting Embodiments of the Invention

In various embodiments, the present invention provides a solid matrix for storing and/or stabilizing and/or preserving a biological sample in a substantially dry state or a dry state, wherein the solid matrix consists essentially of or consists of a matrix material and a buffer, wherein the matrix material is a non-dissolvable dry solid material or a non-dissolvable substantially dry material, and the buffer is impregnated in and/or incorporated in and/or entrained in the matrix material in a substantially dry state or a dry state, and wherein the biological sample comprises one or more nucleic acids.

In various embodiments, the present invention provides a solid matrix for storing and/or stabilizing and/or preserving a biological sample in a substantially dry state or a dry state at ambient temperature or under ambient conditions, wherein the solid matrix consists essentially of or consists of a matrix material and a buffer, wherein the matrix material is a non-dissolvable dry solid material or a non-dissolvable substantially dry material, and the buffer is impregnated in and/or incorporated in and/or entrained in the matrix material in a substantially dry state or a dry state, wherein the biological sample comprises one or more nucleic acids.

In various embodiments, the present invention provides a solid matrix for storing and/or stabilizing and/or preserving a biological sample in a substantially dry state or a dry state, wherein the solid matrix comprises a matrix material and at least one buffer, wherein: the matrix material is a non-dissolvable dry solid material or a non-dissolvable substantially dry material; the buffer is impregnated in and/or incorporated in and/or entrained in the matrix material in a substantially dry state or a dry state; the solid matrix does not comprise a denaturant; and the biological sample comprises one or more nucleic acids.

In various embodiments, the present invention provides a solid matrix for storing and/or stabilizing and/or preserving a biological sample in a substantially dry state or a dry state at ambient temperature or under ambient conditions, wherein the solid matrix comprises a matrix material and at least one buffer, wherein: the matrix material is a non-dissolvable dry solid material or a non-dissolvable substantially dry material; the buffer is impregnated in and/or incorporated in and/or entrained in the matrix material in a substantially dry state or a dry state; the solid matrix does not comprise a denaturant; and the biological sample comprises one or more nucleic acids.

In various embodiments the present invention provides a method for storing and/or stabilizing and/or preserving one or more biological samples on a solid matrix, comprising: contacting the solid matrix with a biological sample, wherein the biological sample comprises one or more nucleic acids; drying the solid matrix containing the biological sample; and storing and/or stabilizing and/or preserving the biological sample on the solid matrix in a substantially dry state or a dry state, wherein the solid matrix comprises a matrix material and at least one buffer, wherein: the matrix material is a non-dissolvable dry solid material or a non-dissolvable substantially dry material; the buffer is impregnated in and/or incorporated in and/or entrained in the matrix material in a substantially dry state or a dry state; and the solid matrix does not comprise a denaturant. In some embodiments, the biological sample is stored and/or stabilized and/or preserved on the solid matrix at ambient temperature or under ambient conditions.

In various embodiments, the present invention provides a method for storing and/or stabilizing and/or preserving one or more biological samples on a solid matrix, comprising: contacting the solid matrix with a biological sample, wherein the biological sample comprises one or more nucleic acids; drying the solid matrix containing the biological sample; and storing and/or stabilizing and/or preserving the biological sample on the solid matrix in a substantially dry state or a dry state, wherein the solid matrix consists essentially of or consists of a matrix material and a buffer, wherein the matrix material is a non-dissolvable dry solid material or a non-dissolvable substantially dry solid material, and the buffer is impregnated in and/or incorporated in and/or entrained in the matrix material in a substantially dry state or a dry state.

In various embodiments, the present invention provides a method for storing and/or stabilizing and/or preserving one or more biological samples on a solid matrix, comprising: contacting the solid matrix with a biological sample, wherein the biological sample comprises one or more nucleic acids; drying the solid matrix containing the biological sample; and storing and/or stabilizing and/or preserving the biological sample on the solid matrix in a substantially dry state or a dry state at ambient temperature or under ambient conditions, wherein the solid matrix consists essentially of or consists of a matrix material and a buffer, wherein the matrix material is a non-dissolvable dry solid material or a non-dissolvable substantially dry solid material, and the buffer is impregnated in and/or incorporated in and/or entrained in the matrix material in a substantially dry state or a dry state.

In various embodiments, the present invention provides a method for storing and/or stabilizing and/or preserving one or more biological samples on a solid matrix, comprising: contacting the solid matrix with a biological sample, wherein the biological sample comprises one or more nucleic acids; drying the solid matrix containing the biological sample; and storing and/or stabilizing and/or preserving the biological sample on the solid matrix in a substantially dry state or a dry state, wherein the solid matrix consists essentially of or consists of a matrix material and two different buffers, wherein the matrix material is a non-dissolvable dry solid material or a non-dissolvable substantially dry solid material, and the buffers are impregnated in and/or incorporated in and/or entrained in the matrix material in a substantially dry state or a dry state. In some embodiments, the biological sample is stored and/or stabilized and/or preserved on the solid matrix at ambient temperature or under ambient conditions.

In various embodiments, the present invention provides a method for storing and/or stabilizing and/or preserving one or more biological samples on a solid matrix, comprising: contacting the solid matrix with a biological sample, wherein the biological sample comprises one or more nucleic acids; drying the solid matrix containing the biological sample; and storing and/or stabilizing and/or preserving the biological sample on the solid matrix in a dry state, wherein the solid matrix consists essentially of or consists of a matrix material and a buffer, wherein the matrix material is a non-dissolvable dry solid material, and the buffer is impregnated in and/or incorporated in and/or entrained in the matrix material in a dry state.

In various embodiments, the present invention provides a method for storing and/or stabilizing and/or preserving one or more biological samples on a solid matrix, comprising: contacting the solid matrix with a biological sample, wherein the biological sample comprises one or more nucleic acids; drying the solid matrix containing the biological sample; and storing and/or stabilizing and/or preserving the biological sample on the solid matrix in a dry state at ambient temperature or under ambient conditions, wherein the solid matrix consists essentially of or consists of a matrix material and a buffer, wherein the matrix material is a non-dissolvable dry solid material, and the buffer is impregnated in and/or incorporated in and/or entrained in the matrix material in a dry state.

In various embodiments, the present invention provides a method for storing and/or stabilizing and/or preserving one or more biological samples on a solid matrix, comprising: contacting the solid matrix with a biological sample, wherein the biological sample comprises one or more nucleic acids; drying the solid matrix containing the biological sample; storing and/or stabilizing and/or preserving the biological sample on the solid matrix in a substantially dry state or a dry state; recovering the biological sample from the solid matrix; and extracting the nucleic acids from the biological sample, wherein the solid matrix consists essentially of or consists of a matrix material and a buffer, wherein the matrix material is a non-dissolvable dry solid material or a non-dissolvable substantially dry solid material, and the buffer is impregnated in and/or incorporated in and/or entrained in the matrix material in a substantially dry state or a dry state. In some embodiments, the method further comprises analyzing the nucleic acids. In some embodiments, the method further comprises analyzing the extracted nucleic acids.

In various embodiments, the present invention provides a method for storing and/or stabilizing and/or preserving one or more biological samples on a solid matrix, comprising: contacting the solid matrix with a biological sample, wherein the biological sample comprises one or more nucleic acids; drying the solid matrix containing the biological sample; storing and/or stabilizing and/or preserving the biological sample on the solid matrix in a substantially dry state or a dry state at ambient temperature or under ambient conditions; recovering the biological sample from the solid matrix; and extracting the nucleic acids from the biological sample, wherein the solid matrix consists essentially of or consists of a matrix material and a buffer, wherein the matrix material is a non-dissolvable dry solid material or a non-dissolvable substantially dry solid material, and the buffer is impregnated in and/or incorporated in and/or entrained in the matrix material in a substantially dry state or a dry state. In some embodiments, the method further comprises analyzing the nucleic acids. In some embodiments, the method further comprises analyzing the extracted nucleic acids.

In various embodiments, the present invention provides a method for storing and/or stabilizing and/or preserving one or more biological samples on a solid matrix, comprising: contacting the solid matrix with a biological sample, wherein the biological sample comprises one or more nucleic acids; drying the solid matrix containing the biological sample; storing and/or stabilizing and/or preserving the biological sample on the solid matrix in a substantially dry state or a dry state; recovering the biological sample from the solid matrix; and extracting the nucleic acids from the biological sample, wherein the solid matrix comprises a matrix material and at least one buffer, wherein: the matrix material is a non-dissolvable dry solid material or a non-dissolvable substantially dry material; the buffer is impregnated in and/or incorporated in and/or entrained in the matrix material in a substantially dry state or a dry state; and the solid matrix does not comprise a denaturant. In some embodiments, the biological sample is stored and/or stabilized and/or preserved on the solid matrix at ambient temperature or under ambient conditions. In some embodiments, the method further comprises analyzing the nucleic acids. In some embodiments, the method further comprises analyzing the extracted nucleic acids.

In various embodiments, the present invention provides a method for storing and/or stabilizing and/or preserving one or more biological samples on a solid matrix, comprising: contacting the solid matrix with a biological sample, wherein the biological sample comprises one or more nucleic acids; drying the solid matrix containing the biological sample; storing and/or stabilizing and/or preserving the biological sample on the solid matrix in a substantially dry state or a dry state; recovering the biological sample from the solid matrix; and extracting the nucleic acids from the biological sample, wherein the solid matrix comprises a matrix material and two different buffers, wherein: the matrix material is a non-dissolvable dry solid material or a non-dissolvable substantially dry material; the buffers are impregnated in and/or incorporated in and/or entrained in the matrix material in a substantially dry state or a dry state; and the solid matrix does not comprise a denaturant. In some embodiments, the biological sample is stored and/or stabilized and/or preserved on the solid matrix at ambient temperature or under ambient conditions. In some embodiments, the method further comprises analyzing the nucleic acids. In some embodiments, the method further comprises analyzing the extracted nucleic acids.

In various embodiments, the present invention provides a method for storing and/or stabilizing and/or preserving one or more biological samples on a solid matrix, comprising: contacting the solid matrix with a biological sample, wherein the biological sample comprises one or more nucleic acids; drying the solid matrix containing the biological sample; storing and/or stabilizing and/or preserving the biological sample on the solid matrix in a substantially dry state or a dry state; recovering the biological sample from the solid matrix; and extracting the nucleic acids from the biological sample, wherein the solid matrix consists essentially of or consists of a matrix material and two different buffers, wherein the matrix material is a non-dissolvable dry solid material or a non-dissolvable substantially dry solid material, and the buffers are impregnated in and/or incorporated in and/or entrained in the matrix material in a substantially dry state or a dry state. In some embodiments, the method further comprises analyzing the nucleic acids.

In various embodiments, the present invention provides a method for storing and/or stabilizing and/or preserving one or more biological samples on a solid matrix, comprising: contacting the solid matrix with a biological sample, wherein the biological sample comprises one or more nucleic acids; drying the solid matrix containing the biological sample; storing and/or stabilizing and/or preserving the biological sample on the solid matrix in a substantially dry state or a dry state, wherein the nucleic acids are extracted from the biological sample and stored and/or stabilized and/or preserved on the solid matrix in a substantially dry state or a dry state; and recovering the nucleic acids from the solid matrix, wherein the solid matrix consists essentially of or consists of a matrix material and a buffer, wherein the matrix material is a non-dissolvable dry solid material or a non-dissolvable substantially dry solid material, and the buffer is impregnated in and/or incorporated in and/or entrained in the matrix material in a substantially dry state. In some embodiments, the method further comprises analyzing the nucleic acids. In some embodiments, the method further comprises analyzing the recovered nucleic acids.

In various embodiments, the present invention provides a method for storing and/or stabilizing and/or preserving one or more biological samples on a solid matrix, comprising: contacting the solid matrix with a biological sample, wherein the biological sample comprises one or more nucleic acids; drying the solid matrix containing the biological sample; storing and/or stabilizing and/or preserving the biological sample on the solid matrix in a substantially dry state or a dry state at ambient temperature or under ambient conditions, wherein the nucleic acids are extracted from the biological sample and stored and/or stabilized and/or preserved on the solid matrix in a substantially dry state or a dry state at ambient temperature or under ambient conditions; and recovering the nucleic acids from the solid matrix, wherein the solid matrix consists essentially of or consists of a matrix material and a buffer, wherein the matrix material is a non-dissolvable dry solid material or a non-dissolvable substantially dry solid material, and the buffer is impregnated in and/or incorporated in and/or entrained in the matrix material in a substantially dry state. In some embodiments, the method further comprises analyzing the nucleic acids. In some embodiments, the method further comprises analyzing the recovered nucleic acids.

In various embodiments, the present invention provides a method for storing and/or stabilizing and/or preserving one or more biological samples on a solid matrix, comprising: contacting the solid matrix with a biological sample, wherein the biological sample comprises one or more nucleic acids; drying the solid matrix containing the biological sample; storing and/or stabilizing and/or preserving the biological sample on the solid matrix in a substantially dry state or a dry state, wherein the nucleic acids are extracted from the biological sample and stored and/or stabilized and/or preserved on the solid matrix in a substantially dry state or a dry state; and recovering the nucleic acids from the solid matrix, wherein the solid matrix comprises a matrix material and at least one buffer, wherein: the matrix material is a non-dissolvable dry solid material or a non-dissolvable substantially dry material; the buffer is impregnated in and/or incorporated in and/or entrained in the matrix material in a substantially dry state or a dry state; and the solid matrix does not comprise a denaturant. In some embodiments, the biological sample is stored and/or stabilized and/or preserved on the solid matrix at ambient temperature or under ambient conditions. In some embodiments, the method further comprises analyzing the nucleic acids. In some embodiments, the method further comprises analyzing the recovered nucleic acids.

In various embodiments, the present invention provides a method for storing and/or stabilizing and/or preserving one or more biological samples on a solid matrix, comprising: contacting the solid matrix with a biological sample, wherein the biological sample comprises one or more nucleic acids; drying the solid matrix containing the biological sample; storing and/or stabilizing and/or preserving the biological sample on the solid matrix in a substantially dry state or a dry state, wherein the nucleic acids are extracted from the biological sample and stored and/or stabilized and/or preserved on the solid matrix in a substantially dry state or a dry state; and recovering the nucleic acids from the solid matrix, wherein the solid matrix comprises a matrix material and two different buffers, wherein: the matrix material is a non-dissolvable dry solid material or a non-dissolvable substantially dry material; the buffers are impregnated in and/or incorporated in and/or entrained in the matrix material in a substantially dry state or a dry state; and the solid matrix does not comprise a denaturant. In some embodiments, the biological sample is stored and/or stabilized and/or preserved on the solid matrix at ambient temperature or under ambient conditions. In some embodiments, the method further comprises analyzing the nucleic acids. In some embodiments, the method further comprises analyzing the recovered nucleic acids.

In various embodiments, the present invention provides a method for storing and/or stabilizing and/or preserving one or more biological samples on a solid matrix, comprising: contacting the solid matrix with a biological sample, wherein the biological sample comprises one or more nucleic acids; drying the solid matrix containing the biological sample; storing and/or stabilizing and/or preserving the biological sample on the solid matrix in a substantially dry state or a dry state, wherein the nucleic acids are extracted from the biological sample and stored and/or stabilized and/or preserved on the solid matrix in a substantially dry state or a dry state; and recovering the nucleic acids from the solid matrix, wherein the solid matrix consists essentially of or consists of a matrix material and two different buffers, wherein the matrix material is a non-dissolvable dry solid material or a non-dissolvable substantially dry solid material, and the buffers are impregnated in and/or incorporated in and/or entrained in the matrix material in a substantially dry state. In some embodiments, the method further comprises analyzing the nucleic acids. In some embodiments, the method further comprises analyzing the recovered nucleic acids.

In various embodiments, the present invention provides a solid matrix for storing and/or stabilizing and/or preserving a biological sample in a substantially dry state or a dry state, where the solid matrix consists essentially of or consists of a matrix material and two different buffers, wherein the matrix material is a non-dissolvable dry solid material or a non-dissolvable substantially dry material, and the two different buffers are impregnated in and/or incorporated in and/or entrained in the matrix material in a substantially dry state or a dry state, and wherein the biological sample comprises one or more nucleic acids.

In various embodiments, the present invention provides a solid matrix for storing and/or stabilizing and/or preserving a biological sample in a substantially dry state or a dry state at ambient temperature or under ambient conditions, where the solid matrix consists essentially of or consists of a matrix material and two different buffers, wherein the matrix material is a non-dissolvable dry solid material or a non-dissolvable substantially dry material, and the two different buffers are impregnated in and/or incorporated in and/or entrained in the matrix material in a substantially dry state or a dry state, and wherein the biological sample comprises one or more nucleic acids.

In various embodiments, the present invention provides a solid matrix for storing and/or stabilizing and/or preserving a biological sample in a substantially dry state or a dry state, where the solid matrix comprises a matrix material and two different buffers, wherein the matrix material is a non-dissolvable dry solid material or a non-dissolvable substantially dry material, and the two different buffers are impregnated in and/or incorporated in and/or entrained in the matrix material in a substantially dry state or a dry state; the solid matrix does not comprise a denaturant; and the biological sample comprises one or more nucleic acids.

Various embodiments of the present invention relate to a nucleic acid stabilization matrix, wherein the matrix is configured to collect, extract, and store one or more nucleic acids from a biological sample for a prolonged period of time, followed by use in various applications. The matrix is configured to store one or more nucleic acids in a substantially dry state at ambient temperature and substantially retain the integrity of the one or more nucleic acids.

Various embodiments of the present invention relate to a biological sample stabilization matrix, wherein the matrix is configured to collect, extract, and store one or biological materials (e.g., nucleic acids, proteins, etc.) from a biological sample for a prolonged period of time, followed by use in various applications. The matrix is configured to store one or more biological samples in a substantially dry state at ambient temperature and substantially retain the integrity of the one or more biological samples Various embodiments of the present invention provide a composition for stabilizing and/or storing and/or preserving one or more nucleic acids on a matrix material, comprising at least one buffer. In some embodiments, the composition further comprises at least one denaturant. In some embodiments, the composition further comprises at least one reducing agent. In some embodiments, the composition further comprises at least one antioxidant. In some embodiments, the composition has a pH of 2.0 to 8.0. In some embodiments, the composition is in a substantially dry state. In some embodiments, the composition is in a dry state.

Various embodiments of the present invention provide a composition for stabilizing and/or storing and/or preserving one or more biological samples on a matrix material, comprising at least one buffer. In some embodiments, the composition further comprises at least one denaturant. In some embodiments, the composition further comprises at least one reducing agent. In some embodiments, the composition further comprises at least one antioxidant. In some embodiments, the composition has a pH of 2.0 to 8.0. In some embodiments, the composition is in a substantially dry state. In some embodiments, the composition is in a dry state. In some embodiments, the composition has a pH of 2.0 to 8.0.

In various embodiments the present invention provides a composition for stabilizing and/or storing and/or preserving one or more biological samples on a matrix material, the composition comprising at least one buffer, with the proviso that the composition does not comprise a denaturant. In some embodiments, the composition further comprises at least one reducing agent. In some embodiments, the composition further comprises at least one antioxidant. In some embodiments the composition has a pH of 2.0 to 8.0.

Various embodiments of the present invention provide a solid matrix, comprising: a matrix material; and at least one buffer impregnated in the matrix material in a substantially dry state, wherein the solid matrix is configured to stabilize one or more nucleic acids from a biological sample in a substantially dry state at ambient temperature. In some embodiments, the solid matrix further comprises at least one denaturant impregnated in the matrix material in a substantially dry state. In some embodiments, the solid matrix further comprises at least one reducing agent impregnated in the matrix material in a substantially dry state. In some embodiments, the solid matrix further comprises at least one antioxidant impregnated in the matrix material in a substantially dry state.

Various embodiments of the present invention provide a solid matrix, comprising: a matrix material; and at least one buffer impregnated in the matrix material in a substantially dry state or a dry state, wherein the matrix material is a non-dissolvable dry solid material or a non-dissolvable substantially dry material, wherein the solid matrix is configured to stabilize one or more nucleic acids in a biological sample in a substantially dry state or a dry state, wherein the solid matrix does not comprise a denaturant. In some embodiments, the solid matrix further comprises at least one reducing agent impregnated in the matrix material in a substantially dry state or a dry state. In some embodiments, the solid matrix further comprises at least one antioxidant impregnated in the matrix material in a substantially dry state or a dry state.

Various embodiments of the present invention provide a solid matrix, comprising: a matrix material; and at least one buffer impregnated therein in a dry state, wherein the solid matrix is configured to stabilize one or more nucleic acids from a biological sample in a substantially dry state at ambient temperature. In some embodiments, the solid matrix further comprises at least one denaturant impregnated in the matrix material in a dry state. In some embodiments, the solid matrix further comprises at least one reducing agent impregnated in the matrix material in a dry state. In some embodiments, the solid matrix further comprises at least one antioxidant impregnated in the matrix material in a dry state.

Various embodiments of the present invention provide a solid matrix, comprising: a matrix material; and at least one buffer impregnated therein in a dry state, wherein the solid matrix is configured to stabilize one or more nucleic acids from a biological sample in a dry state at ambient temperature. In some embodiments, the solid matrix further comprises at least one denaturant impregnated in the matrix material in a dry state. In some embodiments, the solid matrix further comprises at least one reducing agent impregnated in the matrix material in a dry state. In some embodiments, the solid matrix further comprises at least one antioxidant impregnated in the matrix material in a dry state.

Various embodiments of the present invention provide a solid matrix, comprising: a matrix material; and at least one buffer impregnated in the matrix material in a substantially dry state, wherein the solid matrix is configured to stabilize one or more biological samples in a substantially dry state at ambient temperature.

Various embodiments of the present invention provide a solid matrix, comprising: a matrix material; and at least one buffer impregnated in the matrix material in a substantially dry state, wherein the solid matrix is configured to stabilize one or more biological samples in a dry state at ambient temperature.

Various embodiments of the present invention provide a method for stabilizing one or more biological samples on a solid matrix, comprising: a) providing a matrix material; b) contacting the matrix material with a stabilizing composition; c) drying the matrix material contacted with the stabilizing composition to form a stabilized solid matrix; d) treating the stabilized solid matrix with one or more biological samples; e) drying the stabilized solid matrix treated with the one or more biological samples; and f) storing the dried stabilized solid matrix treated with the one or more biological samples under ambient conditions.

Various embodiments of the present invention provide a composition for stabilizing and/or storing and/or preserving one or more nucleic acids on a solid matrix, comprising: at least one buffer; at least one optional denaturant; at least one optional reducing agent; and at least one optional antioxidant, wherein the composition has a pH between 3.0 to 8.0. In some embodiments, the at least one buffer is selected from tris(2-carboxyethyl)phosphine hydrochloride (TCEP-HCl), citric acid, 2-(N-morpholino)ethanesulfonic acid (MES), and 3-(N-morpholino)propanesulfonic acid (MOPS). In some embodiments, the at least one buffer is citric acid. In some embodiments, the at least one optional denaturant is selected from sodium thiocyanate, urea, and thiourea. In some embodiments, the at least one optional reducing agent is tris(2-carboxyethyl)phosphine hydrochloride (TCEP-HCl). In some embodiments, the at least one optional antioxidant is hydroquinone monomethyl ether (MEHQ). In some embodiments, the solid matrix comprises a matrix material. In some embodiments, the matrix material is a cellulosic paper. In some embodiments, the one or more nucleic acids is virus RNA. In some embodiments, the virus RNA is HIV RNA. In some embodiments, the pH is between 3.5 and 7.0. In some embodiments, the composition is in a substantially dry state. In some embodiments, the composition is in a dry state.

Various embodiments of the present invention provide a method for stabilizing one or more nucleic acids on a solid matrix, comprising: a) providing a matrix material; b) contacting the matrix material with a stabilizing composition; c) drying the matrix material contacted with the stabilizing composition to form a stabilized solid matrix; d) treating the stabilized solid matrix with a biological sample, wherein the biological sample comprises one or more nucleic acids; e) drying the stabilized solid matrix treated with the biological sample; and f) storing the dried stabilized solid matrix treated with the biological sample under ambient conditions. In some embodiments, the stabilizing composition comprises, at least one buffer; at least one optional denaturant; at least one optional reducing agent; and at least one optional antioxidant, wherein the stabilizing composition has a pH between 3.0 and 8.0. In some embodiments, the at least one buffer is selected from tris(2-carboxyethyl)phosphine hydrochloride (TCEP-HCl), citric acid, 2-(N-morpholino)ethanesulfonic acid (MES), and 3-(N-morpholino)propanesulfonic acid (MOPS). In some embodiments, the at least one buffer is citric acid. In some embodiments, the at least one optional denaturant is selected from sodium thiocyanate, urea, and thiourea. In some embodiments, the at least one optional antioxidant is hydroquinone monomethyl ether (MEHQ). In some embodiments, the solid matrix is a cellulosic paper. In some embodiments, the biological sample is human plasma. In some embodiments, the one or more nucleic acids is virus RNA. In some embodiments, the virus RNA is HIV RNA. In some embodiments, the pH is between 3.5 and 7.0. In some embodiments, the method further comprises, extracting the one or more nucleic acids from the dried stabilized solid matrix treated with the biological sample. In some embodiments, the method further comprises, analyzing the one or more nucleic acids extracted from the dried stabilized solid matrix.

Various embodiments of the present invention provide a method for stabilizing one or more nucleic acids on a solid matrix, comprising: providing a matrix material; contacting the matrix material with a stabilizing composition; drying the matrix material contacted with the stabilizing composition to form a stabilized solid matrix; treating the stabilized solid matrix with a biological sample, wherein the biological sample comprises one or more nucleic acids; drying the stabilized solid matrix treated with the biological sample;

and storing the dried stabilized solid matrix treated with the biological sample under ambient conditions. In some embodiments, the stabilizing composition comprises at least one buffer, and does not comprise a denaturant. In some embodiments the stabilizing composition further comprises at least one antioxidant. In some embodiments the stabilizing composition further comprises at least one reducing agent.

Various embodiments of the present invention provide a method for stabilizing one or more nucleic acids on a solid matrix, comprising: providing a matrix material; contacting the matrix material with a stabilizing composition; drying the matrix material contacted with the stabilizing composition to form a stabilized solid matrix; treating the stabilized solid matrix with a biological sample, wherein the biological sample comprises one or more nucleic acids; drying the stabilized solid matrix treated with the biological sample; and storing the dried stabilized solid matrix treated with the biological sample under ambient conditions. In some embodiments, the stabilizing composition consists essentially of or consists of a buffer. In some embodiments the stabilizing composition consists essentially of or consists of two different buffers.

Various embodiments of the present invention provide a solid matrix, comprising: at least one buffer impregnated therein in a substantially dry state, wherein the solid matrix is configured to stabilize one or more nucleic acids from a biological sample in a substantially dry state at ambient temperature. In some embodiments, the solid matrix further comprises at least one denaturant impregnated therein in a substantially dry state. In some embodiments, the solid matrix further comprises, at least one reducing agent impregnated therein in a substantially dry state. In some embodiments, the solid matrix further comprises, at least one antioxidant impregnated therein in a substantially dry state. In some embodiments, the at least one buffer is selected from tris(2-carboxyethyl)phosphine hydrochloride (TCEP-HCl), citric acid, 2-(N-morpholino)ethanesulfonic acid (YMS), and 3-(N-morpholino)propanesulfonic acid (MOPS). In some embodiments, the at least one buffer is citric acid. In some embodiments, the at least one denaturant is selected from sodium thiocyanate, urea, and thiourea. In some embodiments, the at least one antioxidant is hydroquinone monomethyl ether (MEHQ). In some embodiments, the solid matrix is a cellulosic paper. In some embodiments, the biological sample is human plasma. In some embodiments, the one or more nucleic acids is virus RNA. In some embodiments, the virus RNA is HIV RNA. In some embodiments, the at least one buffer has a pH between 3.0 and 8.0. In some embodiments, the pH is between 3.5 and 7.0.

Kits

The exact nature of the components configured in the inventive kit depends on its intended purpose. In one embodiment, the kit is configured for human subjects. In further embodiments, the kit is configured for research and/or veterinary applications, treating subjects such as, but not limited to, farm animals, domestic animals, and laboratory animals (e.g., mouse or mice).

Instructions for use may be included in the kit. "Instructions for use" typically include a tangible expression describing the technique to be employed in using the components of the kit to effect a desired outcome (e.g., allowing accurate diagnostic and evaluation of therapy efficacy in patients with low HIV viral load). Optionally, the kit also contains other useful components, such as measuring tools, diluents, elution buffers, syringes or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, dried, substantially dried, or lyophilized form; they can be provided at ambient, room, refrigerated or frozen temperatures, or under ambient conditions. The components are typically contained in suitable packaging material(s). As employed herein, the phrase "packaging material" refers to one or more physical structures used to house the contents of the kit, such as inventive compositions and the like. The packaging material is constructed by well-known methods, to provide a sterile, contaminant-free environment. As used herein, the term "package" refers to a suitable material such as glass, plastic, paper, foil, and the like, capable of holding the individual kit components. The packaging material generally has an external label which indicates the contents and/or purpose of the kit and/or its components.

In various embodiments, the present invention provides a kit, comprising: a solid matrix, where the solid matrix comprises a matrix material and at least one buffer, wherein the matrix material is a non-dissolvable dry solid material or a non-dissolvable substantially dry solid material, and the buffer is impregnated in the matrix material in a substantially dry state or a dry state, provided that the solid matrix does not comprise a denaturant; instructions for using the kit; and reagents and instructions for sample processing and preparation.

In various embodiments, the present invention provides a kit, comprising: a solid matrix, where the solid matrix comprises a matrix material and two different buffers, wherein the matrix material is a non-dissolvable dry solid material or a non-dissolvable substantially dry solid material, and the buffers are impregnated in the matrix material in a substantially dry state or a dry state, provided that the solid matrix does not comprise a denaturant; instructions for using the kit; and reagents and instructions for sample processing and preparation.

In various embodiments, the present invention provides a kit for storing and/or preserving and/or stabilizing a biological sample in a substantially dry state or a dry state, the kit comprising: a solid matrix, where the solid matrix comprises a matrix material and at least one buffer, wherein the matrix material is a non-dissolvable dry solid material or a non-dissolvable substantially dry solid material, and the buffer is impregnated in and/or incorporated in and/or entrained in in the matrix material in a substantially dry state or a dry state, provided that the solid matrix does not comprise a denaturant; instructions for using the kit; and reagents and instructions for sample processing and preparation.

In various embodiments, the present invention provides a kit for storing and/or preserving and/or stabilizing a biological sample in a substantially dry state or a dry state, the kit comprising: a solid matrix, where the solid matrix comprises a matrix material and two different buffers, wherein the matrix material is a non-dissolvable dry solid material or a non-dissolvable substantially dry solid material, and the buffers are impregnated in and/or incorporated in and/or entrained in in the matrix material in a substantially dry state or a dry state, provided that the solid matrix does not comprise a denaturant; instructions for using the kit; and reagents and instructions for sample processing and preparation. In some embodiments, the biological sample is stored and/or preserved and/or stabilized at ambient temperature or under ambient conditions.

In various embodiments, the present invention provides a kit for storing and/or preserving and/or stabilizing a biological sample in a substantially dry state or a dry state at ambient temperature or under ambient conditions, the kit comprising: a solid matrix, where the solid matrix comprises a matrix material and at least one buffer, wherein the matrix material is a non-dissolvable dry solid material or a non-dissolvable substantially dry solid material, and the buffer is impregnated in and/or incorporated in and/or entrained in in the matrix material in a substantially dry state or a dry state, provided that the solid matrix does not comprise a denaturant; instructions for using the kit; and reagents and instructions for sample processing and preparation.

In various embodiments, the present invention provides a kit, comprising: a solid matrix, where the solid matrix consists essentially of or consists of a matrix material and a buffer, wherein the matrix material is a non-dissolvable dry solid material or a non-dissolvable substantially dry solid material, and the buffer is impregnated in the matrix material in a substantially dry state or a dry state; instructions for using the kit; and reagents and instructions for sample processing and preparation.

In various embodiments, the present invention provides a kit, comprising: a solid matrix, where the solid matrix consists essentially of or consists of a matrix material and two different buffers, wherein the matrix material is a non-dissolvable dry solid material or a non-dissolvable substantially dry solid material, and the buffers are impregnated in the matrix material in a substantially dry state or a dry state; instructions for using the kit; and reagents and instructions for sample processing and preparation.

In various embodiments, the present invention provides a kit for storing and/or preserving and/or stabilizing a biological sample in a substantially dry state or a dry state, the kit comprising: a solid matrix, where the solid matrix consists essentially of or consists of a matrix material and a buffer, wherein the matrix material is a non-dissolvable dry solid material or a non-dissolvable substantially dry solid material, and the buffer is impregnated in and/or incorporated in and/or entrained in in the matrix material in a substantially dry state or a dry state; instructions for using the kit; and reagents and instructions for sample processing and preparation.

In various embodiments, the present invention provides a kit for storing and/or preserving and/or stabilizing a biological sample in a substantially dry state or a dry state, the kit comprising: a solid matrix, where the solid matrix consists essentially of or consists of a matrix material and two different buffers, wherein the matrix material is a non-dissolvable dry solid material or a non-dissolvable substantially dry solid material, and the buffers are impregnated in and/or incorporated in and/or entrained in in the matrix material in a substantially dry state or a dry state; instructions for using the kit; and reagents and instructions for sample processing and preparation.

In various embodiments, the present invention provides a kit for storing and/or preserving and/or stabilizing a biological sample in a substantially dry state or a dry state at ambient temperature or under ambient conditions, the kit comprising: a solid matrix, where the solid matrix consists essentially of or consists of a matrix material and a buffer, wherein the matrix material is a non-dissolvable dry solid material or a non-dissolvable substantially dry solid material, and the buffer is impregnated in and/or incorporated in and/or entrained in in the matrix material in a substantially dry state or a dry state; instructions for using the kit; and reagents and instructions for sample processing and preparation.

Other features and embodiments of the present invention include one or more of the following numbered paragraphs:

1. A solid matrix for storing a biological sample in a substantially dry state or a dry state, wherein the solid matrix comprises a matrix material and at least one buffer, wherein:
the matrix material is a non-dissolvable dry solid material;
the buffer is impregnated in the matrix material in a substantially dry state or a dry state;
the solid matrix does not comprise a denaturant; and
the biological sample comprises one or more nucleic acids 2. The solid matrix of paragraph 1, wherein the solid matrix further comprises at least one reducing agent, wherein the reducing agent is impregnated in the matrix material in a substantially dry state.

3. The solid matrix of paragraph 2, wherein the reducing agent is dithiothreitol (DTT), 2-mercaptoethanol (2-ME), 2-mercaptoethylamine, or cysteine.

4. The solid matrix of paragraph 1, wherein the solid matrix further comprises at least one antioxidant, wherein the antioxidant is impregnated in the matrix material in a substantially dry state.

5. The solid matrix of paragraph 4, wherein the antioxidant is hydroquinone monomethyl ether (MEHQ), hydroquinone (HQ), or toluhydroquinone (THQ).

6. The solid matrix of paragraph 1, wherein the non-dissolvable dry solid material is a cellulosic paper.

7. The solid matrix of paragraph 1, wherein the buffer is selected from citric acid, tris(2-carboxyethyl)phosphine hydrochloride (TCEP-HCl), oxidized form of tris(2-carboxyethyl)phosphine hydrochloride (TCEPO-HCl), 2-amino-2-hydroxymethyl-propane-1,3-diol (Tris), 2-(N-morpholino)ethanesulfonic acid (MES), 3-(N-morpholino)propanesulfonic acid (MOPS), 4-(2-hydroxyethyl)-1-piperazineethanesulfonic acid (HEPES), phosphate buffers, acetic acid, ascorbic acid, sulfosalicylic acid, formic acid, glycine, glycine-glycine, malic acid, and succinic acid.

8. The solid matrix of paragraph 1, wherein the buffer has a pH of 2.0 to 8.0.

9. The solid matrix of paragraph 1, wherein the biological sample is blood, serum, plasma, tissue, saliva, cells, synovial fluids, urine, or semen.

10. A method for storing one or more biological samples on a solid matrix of claim 1, comprising:
contacting the solid matrix with a biological sample, wherein the biological sample comprises one or more nucleic acids;
drying the solid matrix containing the biological sample; and
storing the biological sample on the solid matrix in a substantially dry state or a dry state.

11. The method of paragraph 10, further comprising recovering the biological sample from the solid matrix.

12. The method of paragraph 11, further comprising extracting the nucleic acids from the biological sample.

13. The method of paragraph 10, wherein the nucleic acids are extracted from the biological sample and stored on the solid matrix in a substantially dry state or a dry state.

14. The method of paragraph 13, further comprising recovering the nucleic acids from the solid matrix.

15. The method of paragraph 10, wherein the non-dissolvable dry solid material is a cellulosic paper.

16. The method of paragraph 10, wherein the buffer is selected from citric acid, tris(2-carboxyethyl)phosphine hydrochloride (TCEP-HCl), oxidized form of tris(2-carboxyethyl)phosphine hydrochloride (TCEPO-HCl), 2-amino-2-hydroxymethyl-propane-1,3-diol (Tris), 2-(N-morpholino)ethanesulfonic acid (MES), 3-(N-morpholino)

propanesulfonic acid (MOPS), 4-(2-hydroxyethyl)-1-piperazineethanesulfonic acid (HEPES), phosphate buffers, acetic acid, ascorbic acid, sulfosalicylic acid, formic acid, glycine, glycine-glycine, malic acid, and succinic acid.

17. The method of paragraph 10, wherein the buffer has a pH of 2.0 to 8.0.

18. The method of paragraph 10, wherein the biological sample is blood, serum, plasma, tissue, saliva, cells, synovial fluids, urine, or semen.

19. The method of paragraph 10, wherein the nucleic acids are RNA.

20. The method of paragraph 10, wherein the nucleic acids are virus RNA.

Non-Limiting Benefits of the Invention

In various embodiments, it was found that HIV RNA recovered from inactivated HIV virus spiked in human plasma (i.e., iHIV virus manually added to human plasma) could be stabilized after drying on cellulosic paper when the paper was first coated with formulations comprising low pH buffer. In some embodiments, the addition of a denaturant and other additives such as another buffer show similar results. In some embodiments, further addition of a reducing agent and a UV protectant/radical trap/antioxidant could be beneficial to increase the stability of HIV RNA. In various embodiments, it was found that HIV RNA recovered from inactivated HIV virus spiked in human plasma (i.e., iHIV virus manually added to human plasma) could be stabilized after drying on cellulosic paper when the paper was first coated with formulations consisting essentially of or consisting of a low pH buffer. In various embodiments, it was found that HIV RNA recovered from inactivated HIV virus spiked in human plasma (i.e., iHIV virus manually added to human plasma) could be stabilized after drying on cellulosic paper when the paper was first coated with formulations comprising a low pH buffer, wherein the formulation did not comprise a denaturant.

In various embodiments, from the commercially available Whatman® 903 paper, small discs (12 mm) were made using a punching device and soaked into the formulations for 1 to 2 minutes. Excess of formulation was removed by quickly touching the soaked discs on a piece of paper. The discs were then transferred to a clean reservoir and dried overnight in a laminar flow hood. Once dried, human plasma spiked with inactivated HIV virus (12,000 viral particles) (i.e., iHIV virus manually added to human plasma) was added to the coated discs and dried overnight in a laminar flow hood. Once dried, the discs were stored in sealed pouches containing a desiccant to keep the moisture low and placed in a 45° C. or 50° C. incubator for several weeks. After the desired amount of time, the discs were removed and the RNA from HIV virus was recovered and quantified by quantitative PCR. After only a few days, it was observed that HIV RNA levels degraded in unprotected samples compared to samples processed at time 0 and stored at 25° C. In some embodiments, discs soaked with the formulations described herein were able to preserve HIV RNA levels upon incubation at 45° C. (or 50° C.) in similar levels to time 0 samples even after 4 weeks at elevated temperature.

Figure 3:
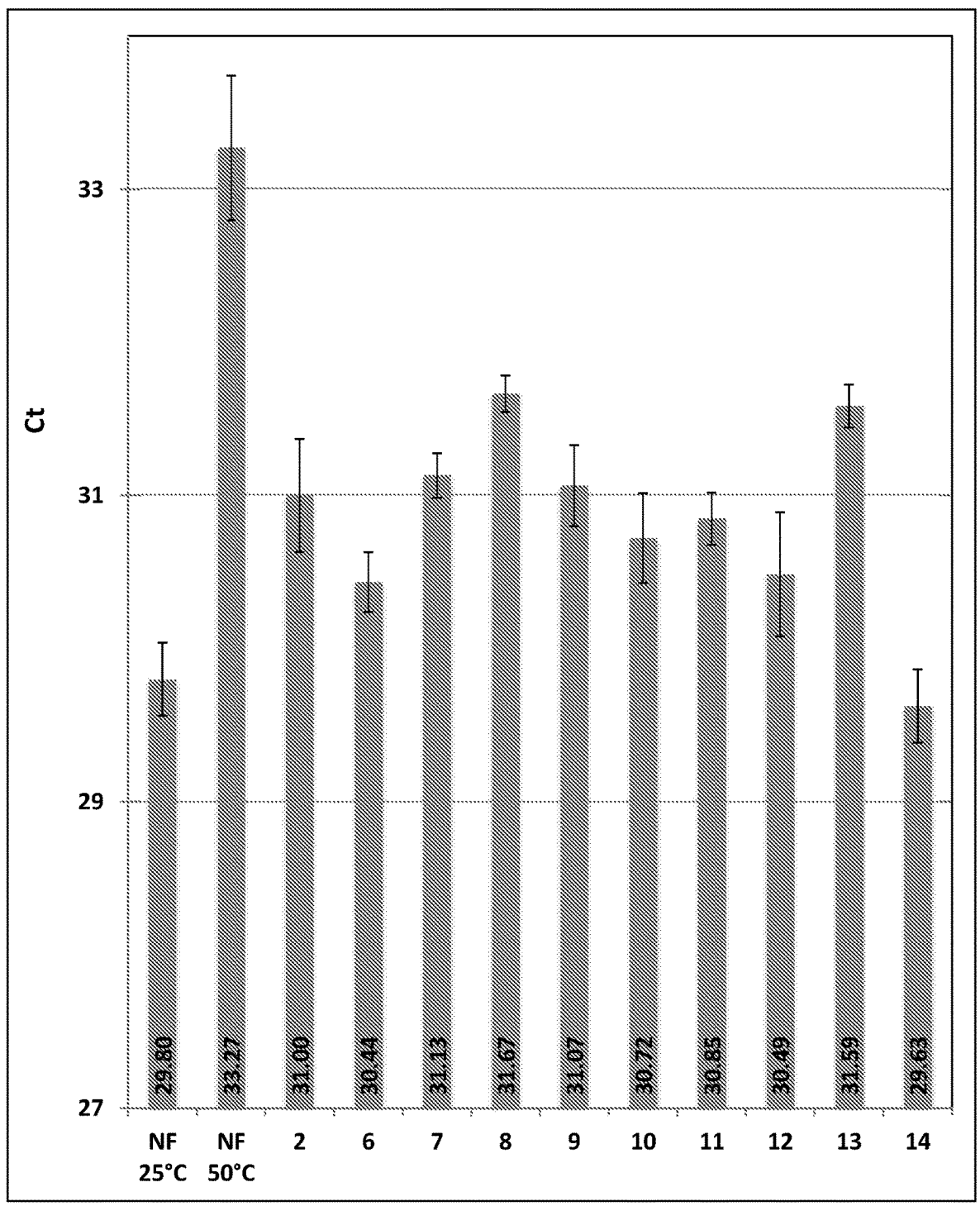
FIG. 3 depicts in accordance with various embodiments of the invention, HIV RNA recovery from Whatman® 903 paper stored at 25° C. and 50° C. for 24 days, where Ct (cycle thresholds) values for protected Whatman® 903 papers soaked in Formulations 2, 6, 7, 8, 9, 10, 11, 12, 13, and 14 (Table 1) at 50° C. were compared with unprotected Whatman® 903 paper soaked in water (no formulation, NF 50° C.) and with unprotected Whatman® 903 paper soaked in water (no formulation, NF 25° C.).
Figure 4:
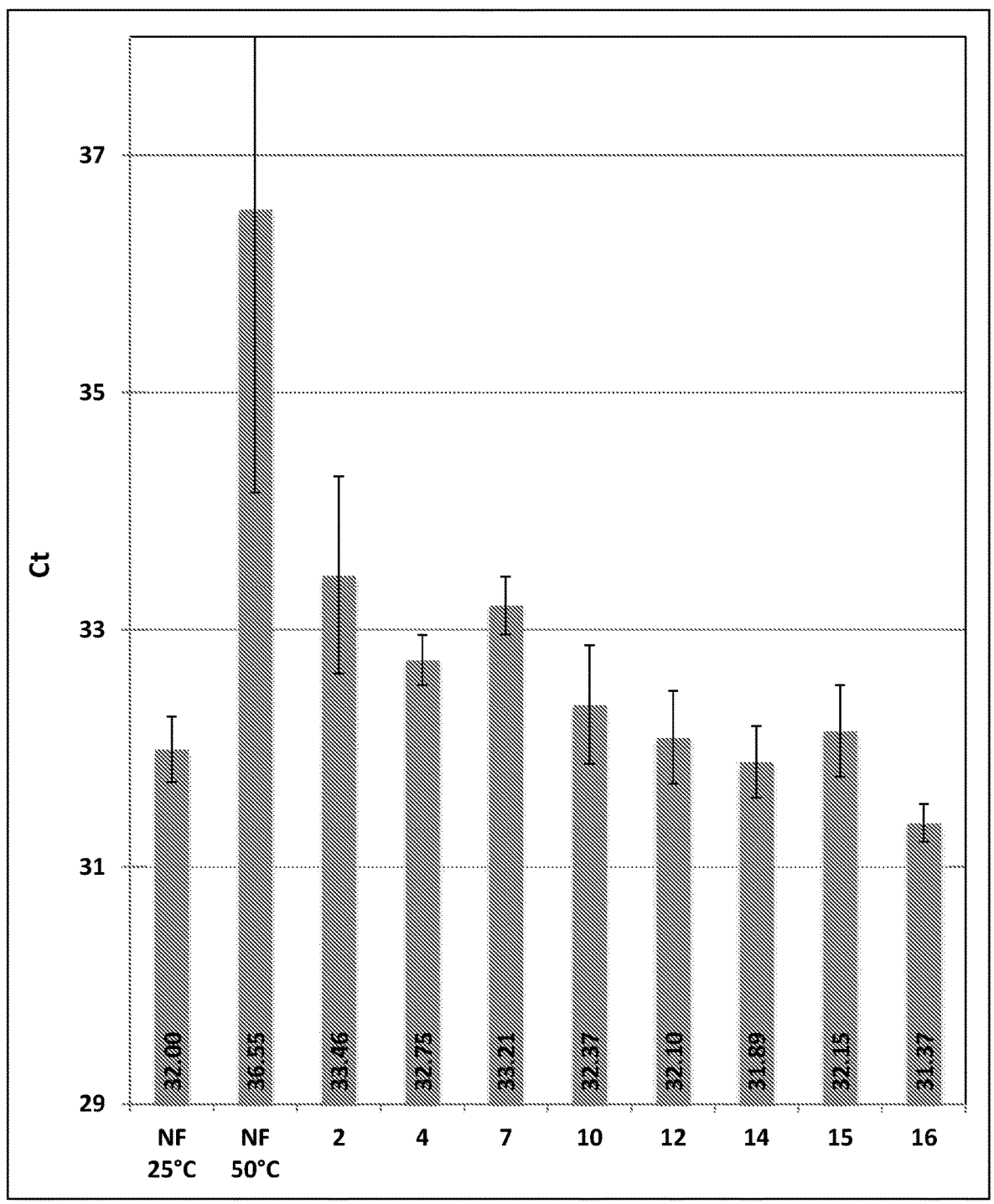
FIG. 4 depicts in accordance with various embodiments of the invention, HIV RNA recovery from Whatman® 903 paper stored at 25° C. and 50° C. for 28 days, where Ct (cycle thresholds) values for protected Whatman® 903 papers soaked in Formulations 2, 4, 7, 10, 12, 14, 15, and 16 (Table 1) at 50° C. were compared with unprotected Whatman® 903 paper soaked in water (no formulation, NF 50° C.) and with unprotected Whatman® 903 paper soaked in water (no formulation, NF 25° C.).
Figure 5:
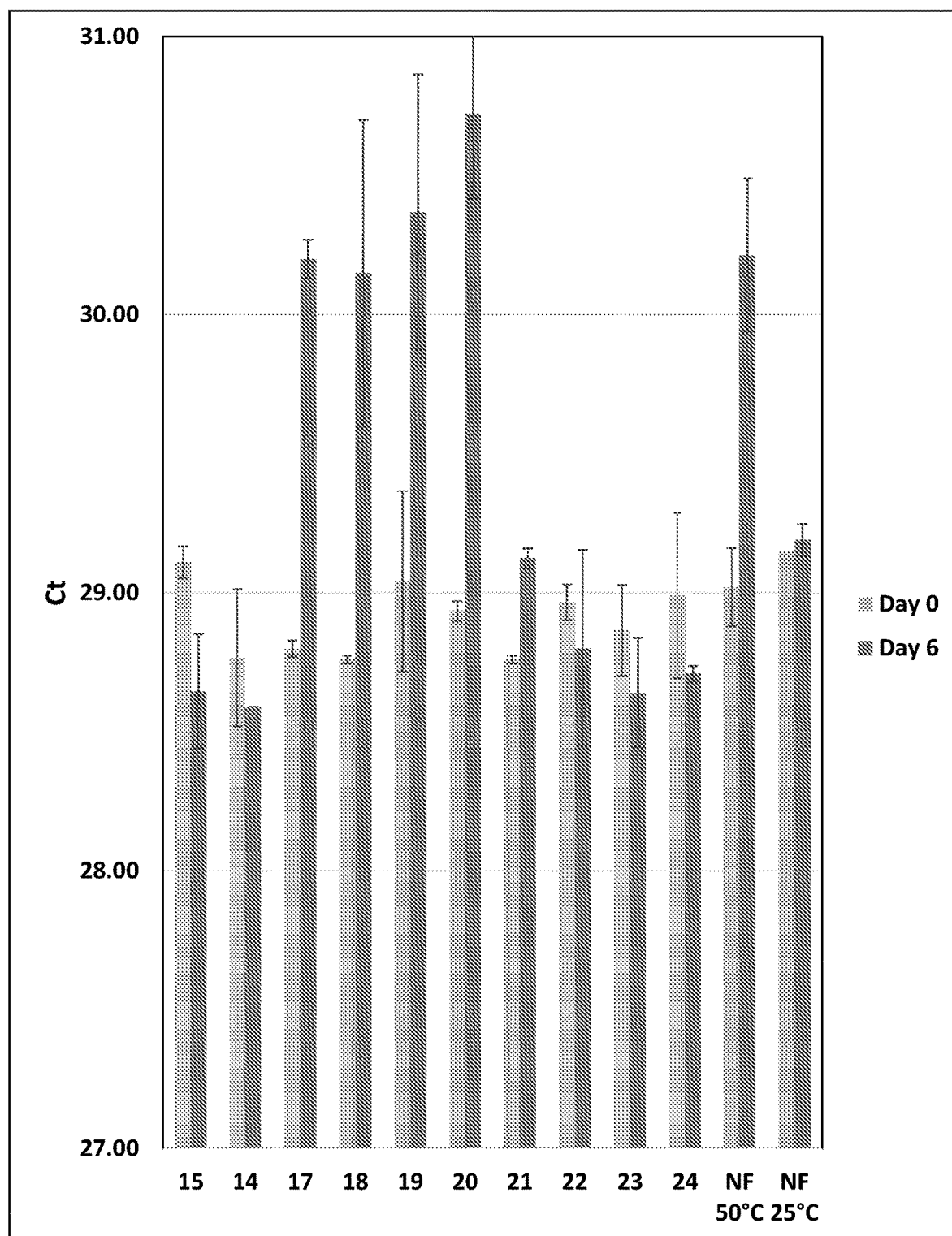
FIG. 5 depicts in accordance with various embodiments of the invention, HIV RNA recovery from Whatman® 903 paper stored at 25° C. and 50° C. for 6 days at 40% relative humidity, where Ct (cycle thresholds) values for protected Whatman® 903 papers soaked in Formulations 14, 15, 17, 18, 19, 20, 21, 22, 23, and 24 (Table 1) at 50° C. were compared with unprotected Whatman® 903 paper soaked in water (no formulation, NF 50° C.) and with unprotected Whatman® 903 paper soaked in water (no formulation, NF 25° C.).

Surprisingly, in various embodiments, cellulosic paper soaked with formulations comprising one or more buffers in the absence of denaturant were able to preserve HIV RNA levels upon incubation at 50° C. in similar levels to time 0 disks stored at 25° C., even after several weeks at elevated temperature (see FIG. 3 and FIG. 4 and FIG. 5). Also surprisingly, in various embodiments, cellulosic paper soaked with formulations consisting essentially of one or two buffers (or consisting of one or two buffers) in the absence of denaturant and/or antioxidant and/or reducing agent were able to preserve HIV RNA levels upon incubation at 50° C. in similar levels to time 0 disks stored at 25° C., even after several weeks at elevated temperature (see FIG. 3 and FIG. 4 and FIG. 5).

EXAMPLES

The following examples are not intended to limit the scope of the claims to the invention, but are rather intended to be exemplary of certain embodiments. Any variations in the exemplified methods which occur to the skilled artisan are intended to fall within the scope of the present invention.

The invention will be further explained by the following examples, which are intended to be purely exemplary of the invention, and should not be considered as limiting the invention in any way. The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1. General Procedure for Preparation of Whatman® 903 and PerkinElmer™ 226 12 mm Discs Containing Formulation Discs of 12 mm size were prepared using a punching device. Up to 15 discs were placed on a 10 cm dish and 3 ml of formulation was added. The discs were soaked for 1 min and the excess of formulation on the discs was removed by rapidly touching the individual filters on a piece of paper. The discs were transferred to a clean 10 cm dish on upward position to dry overnight at ambient temperature in a laminar flow cabinet. After 24 h, the discs were transferred to a 24-well plate and 95 µl of inactivated HIV (iHIV) diluted in human plasma (125,000 viral particles/ml) was spotted on each disc. Discs containing iHIV were then dried at ambient temperature in a laminar flow cabinet for 24 h. The 24-well plates were then sealed in a foil pouch containing 1 desiccant per bag, and incubated at 25° C., 45° C. or 50° C. for 7, 14, 28, 30 and/or 60 days. All experiments were performed using at least 2 replicates for each condition.

Example 2. General Procedure for Virus RNA Purification

HIV RNA was recovered from the discs using 500 µl of elution buffer (2% DTT, 5% polidocanol, 4 M guanidine thiocyanate, 50 mM sodium citrate, pH 5.8) by incubation at 37° C. while shaking (220 rpm) for 90 min. Eluates were harvested at 14,000 rpm for 5 min to remove any paper debris, and 200 µl was used for HIV RNA purification using the QIAamp MinElute virus spin kit (Qiagen), according to manufacturer instructions. HIV RNA was eluted in 50 µl of elution buffer.

Example 3. General Procedure for Virus RNA Quantification by qRT-PCR qRT-PCR was performed on a LightCycler 96 using 12.475 µl of HIV RNA in duplicates in a final reaction volume of 20 containing 0.4 µM of primers (internal), 0.1 µM primer probe (internal), 0.125 µl of HawkZ05 enzyme (Roche), 4 µl of enzyme 5× buffer (internal), and 1.5 mM MnOAc. Amplification was performed by incubating the reactions at 52° C. for 5 min, 55° C. for 5 min, 60° C. for 10 min, 65° C. for 5 min and 45 cycles of 94° C. for 10 s, and 60° C. for 1 min.

Example 4. HIV RNA Recovery from Whatman® 903 Paper at 45° C. for 30 Days

Formulations 1, 2, 3, 4, and 5 (Table 1) were sorbed and dried on Whatman® 903 paper according to the protocol described in Example 1 herein. Inactivated HIV virus (iHIV virus) diluted in human plasma was subsequently added to the Whatman® 903 papers treated with Formulations 1, 2, 3, 4, and 5, dried, and the papers were stored in sealed foil pouches containing a desiccant for 30 days at 45° C. according to the protocol described in Example 1 herein (Formulations 1, 2, 3, 4, and 5). As a control, water (no formulation) was sorbed and dried on Whatman® 903 paper according to the protocol described in Example 1 herein, and inactivated HIV virus (iHIV virus) diluted in human plasma was subsequently added to the unprotected Whatman® 903 paper, dried, and the paper was stored in sealed foil pouches containing desiccant for 30 days at 45° C. according to the protocol described in Example 1 herein (no formulation, NF 45° C.). As a reference, water (no formulation) was sorbed and dried on Whatman® 903 paper according to the protocol described in Example 1 herein, and inactivated HIV virus (iHIV virus) diluted in human plasma was subsequently added to the unprotected Whatman® 903 paper, dried, and the paper was stored in sealed foil pouches containing desiccant for 30 days at 25° C. according to the protocol described in Example 1 herein (no formulation, NF 25° C.). HIV RNA was recovered from the Whatman® 903 papers according to the protocol described in Example 2 herein. After recovery, virus RNA quantification by qRT-PCR was done to determine the levels of HIV RNA using the protocol described in Example 3 herein. Ct (cycle thresholds) values for protected Whatman® 903 papers soaked in Formulations 1, 2, 3, 4, and 5 (Table 1) were compared with unprotected paper soaked in water (no formulation, NF 45° C.) and with unprotected paper soaked in water (no formulation, NF 25° C.) (see FIG. 1). The unprotected paper incubated at 25° C. (no formulation, NF 25° C.) served as reference with Ct values similar to a fresh sample (see FIG. 1).

Figure 2:
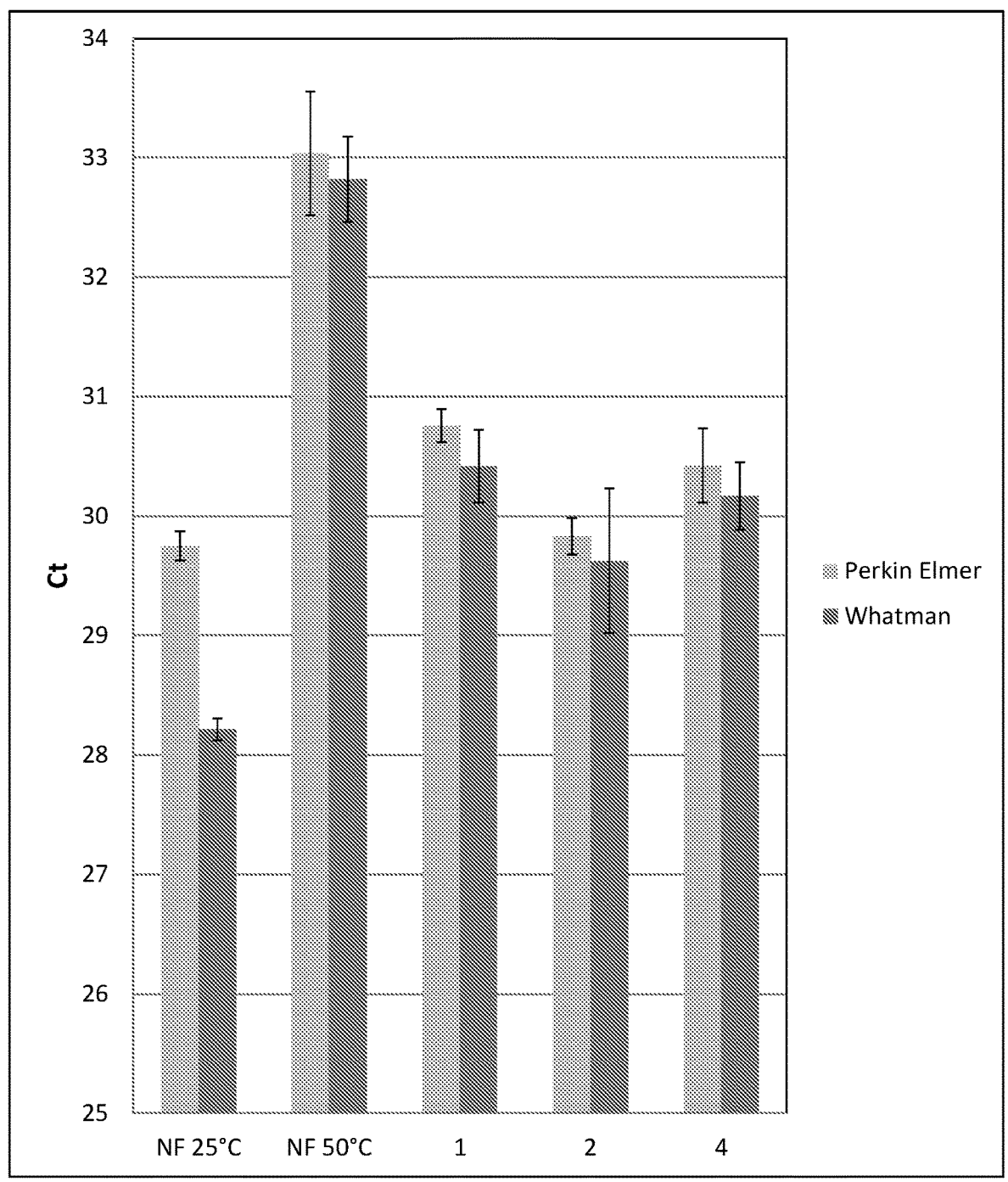
FIG. 2 depicts in accordance with various embodiments of the invention, HIV RNA recovery from Perkin-Elmer™ 226 paper or Whatman® 903 paper stored at 25° C. and 50° C. for 30 days, where Ct (cycle thresholds) values for protected Perkin-Elmer™ 226 papers and Whatman® 903 papers soaked in Formulations 1, 2, and 4 (Table 1) at 50° C. were compared with unprotected Perkin-Elmer™ 226 paper and Whatman® 903 paper soaked in water (no formulation, NF 50° C.) and with unprotected Perkin-Elmer™ 226 paper and Whatman® 903 paper soaked in water (no formulation, NF 25° C.).

Example 5. HIV RNA Recovery from Perkin-Elmer™ 226 Paper or Whatman® 903 Paper Stored at 50° C. for 30 Days Formulations 1, 2, and 4 (Table 1) were sorbed and dried on Perkin-Elmer™ 226 papers or Whatman® 903 papers according to the protocol described in Example 1 herein. Inactivated HIV virus (iHIV virus) diluted in human plasma was subsequently added to the Perkin-Elmer™ 226 papers or Whatman® 903 papers treated with Formulations 1, 2, and 4, dried, and the papers were stored in sealed foil pouches containing a desiccant for 30 days at 50° C. according to the protocol described in Example 1 herein (Formulations 1, 2, and 4). As a control, water (no formulation) was sorbed and dried on Perkin-Elmer™ 226 paper and Whatman® 903 paper according to the protocol described in Example 1 herein, and inactivated HIV virus (iHIV virus) diluted in human plasma was subsequently added to the unprotected Perkin-Elmer™ 226 paper and Whatman® 903 paper, dried, and the papers were stored in sealed foil pouches containing desiccant for 30 days at 50° C. according to the protocol described in Example 1 herein (no formulation, NF 50° C.). As a reference, water (no formulation) was sorbed and dried on Perkin-Elmer™ 226 paper and Whatman® 903 paper according to the protocol described in Example 1 herein, and inactivated HIV virus (iHIV virus) diluted in human plasma was subsequently added to the unprotected Perkin-Elmer™ 226 paper and Whatman® 903 paper, dried, and the papers were stored in sealed foil pouches containing desiccant for 30 days at 25° C. according to the protocol described in Example 1 herein (no formulation, NF 25° C.). HIV RNA was recovered from the Perkin-Elmer™ 226 papers and Whatman® 903 papers according to the protocol described in Example 2 herein. After recovery, virus RNA quantification by qRT-PCR was done to determine the levels of HIV RNA using the protocol described in Example 3 herein. Ct (cycle thresholds) values for protected Perkin-Elmer™ 226 papers and Whatman® 903 papers soaked in Formulations 1, 2, and 4 (Table 1) were compared with unprotected Perkin-Elmer™ 226 paper and Whatman® 903 paper soaked in water (no formulation, NF 50° C.) and with unprotected Perkin-Elmer™ 226 paper and Whatman® 903 paper soaked in water (no formulation, NF 25° C.) (see FIG. 2). The unprotected paper incubated at 25° C. (no formulation, NF 25° C.) served as reference with Ct values similar to a fresh sample (see FIG. 2).

Example 6. HIV RNA Recovery from Whatman® 903 Paper Stored at 50° C. for 24 Days Formulations 2, 6, 7, 8, 9, 10, 11, 12, 13 and 14 (Table 1) were sorbed and dried on Whatman® 903 paper according to the protocol described in Example 1 herein. Inactivated HIV virus (iHIV virus) diluted in human plasma was subsequently added to the Whatman® 903 papers treated with Formulations 2, 6, 7, 8, 9, 10, 11, 12, 13 and 14, dried, and the papers were stored in sealed foil pouches containing a desiccant for 24 days at 50° C. according to the protocol described in Example 1 herein (Formulations 2, 6, 7, 8, 9, 10, 11, 12, 13 and 14). As a control, water (no formulation) was sorbed and dried on Whatman® 903 paper according to the protocol described in Example 1 herein, and inactivated HIV virus (iHIV virus) diluted in human plasma was subsequently added to the unprotected Whatman® 903 paper, dried, and the papers were stored in sealed foil pouches containing desiccant for 24 days at 50° C. according to the protocol described in Example 1 herein (no formulation, NF 50° C.). As a reference, water (no formulation) was sorbed and dried on Whatman® 903 paper according to the protocol described in Example 1 herein, and inactivated HIV virus (iHIV virus) diluted in human plasma was subsequently added to the unprotected Whatman® 903 paper, dried, and the papers were stored in sealed foil pouches containing desiccant for 24 days at 25° C. according to the protocol described in Example 1 herein (no formulation, NF 25° C.). HIV RNA was recovered from the Whatman® 903 papers according to the protocol described in Example 2 herein. After recovery, virus RNA quantification by qRT-PCR was done to determine the levels of HIV RNA using the protocol described in Example 3 herein. Ct (cycle thresholds) values for protected Whatman® 903 papers soaked in Formulations 2, 6, 7, 8, 9, 10, 11, 12, 13, and 14 (Table 1) were compared with unprotected Whatman® 903 paper soaked in water (no formulation, NF 50° C.) and with unprotected Whatman® 903 paper soaked in water (no formulation, NF 25° C.) (see FIG. 3). The unprotected paper incubated at 25° C. (no formulation, NF 25° C.) served as reference with Ct values similar to a fresh sample (see FIG. 3).

Example 7. HIV RNA Recovery from Whatman® 903 Paper Stored at 50° C. for 28 Days Formulations 2, 4, 7, 10, 12, 14, 15, and 16 (Table 1) were sorbed and dried on Whatman® 903 papers according to the protocol described in Example 1 herein. Inactivated HIV virus (iHIV virus) diluted in human plasma was subsequently added to the Whatman® 903 papers treated with Formulations 2, 4, 7, 10, 12, 14, 15, and 16, dried, and the papers were stored in sealed foil pouches containing a desiccant for 28 days at 50° C. according to the protocol described in Example 1 herein (Formulations 2, 4, 7, 10, 12, 14, 15, and 16). As a control, water (no formulation) was sorbed and dried on Whatman® 903 paper according to the protocol described in Example 1 herein, and inactivated HIV virus (iHIV virus) diluted in human plasma was subsequently added to the unprotected Whatman® 903 paper, dried, and the papers were stored in sealed foil pouches containing desiccant for 28 days at 50° C. according to the protocol described in Example 1 herein (no formulation, NF 50° C.). As a reference, water (no formulation) was sorbed and dried on Whatman® 903 paper according to the protocol described in Example 1 herein, and inactivated HIV virus (iHIV virus) diluted in human plasma was subsequently added to the unprotected Whatman® 903 paper, dried, and the papers were stored in sealed foil pouches containing desiccant for 28 days at 25° C. according to the protocol described in Example 1 herein (no formulation, NF 25° C.). HIV RNA was recovered from the Whatman® 903 papers according to the protocol described in Example 2 herein. After recovery, virus RNA quantification by qRT-PCR was done to determine the levels of HIV RNA using the protocol described in Example 3 herein. Ct (cycle thresholds) values for protected Whatman® 903 papers soaked in Formulations 2, 4, 7, 10, 12, 14, 15, and 16 (Table 1) were compared with unprotected Whatman® 903 paper soaked in water (no formulation, NF 50° C.) and with unprotected Whatman® 903 paper soaked in water (no formulation, NF 25° C.) (See FIG. 4). The unprotected paper incubated at 25° C. (no formulation, NF 25° C.) served as reference with Ct values similar to a fresh sample (See FIG. 4).

Example 8. HIV RNA Recovery from Whatman® 903 Paper Stored at 50° C. for 6 Days at 40% Relative Humidity Formulations 14, 15, 17, 18, 19, 20, 21, 22, 23, and 24 (Table 1) were sorbed and dried on Whatman® 903 papers according to the protocol described in Example 1 herein. Inactivated HIV virus (iHIV virus) diluted in human plasma was subsequently added to the Whatman® 903 papers treated with Formulations 14, 15, 17, 18, 19, 20, 21, 22, 23, and 24, dried and the papers were stored in unsealed foil pouches for 6 days at 50° C. at 40% relative humidity. As a control, water (no formulation) was sorbed and dried on Whatman® 903 paper according to the protocol described in Example 1 herein, and inactivated HIV virus (iHIV virus) diluted in human plasma was subsequently added to the unprotected Whatman® 903 paper, dried, and the papers were stored in unsealed foil pouches for 6 days at 50° C. at 40% relative humidity according to the protocol described in Example 1 herein (no formulation, NF 50° C.). As a reference, water (no formulation) was sorbed and dried on Whatman® 903 paper according to the protocol described in Example 1 herein, and inactivated HIV virus (iHIV virus) diluted in human plasma was subsequently added to the unprotected Whatman® 903 paper, dried, and the papers were stored in sealed foil pouches containing desiccant for 6 days at 25° C. according to the protocol described in Example 1 herein (no formulation, NF 25° C.). HIV RNA was recovered from the Whatman® 903 papers according to the protocol described in Example 2 herein. After recovery, virus RNA quantification by qRT-PCR was done to determine the levels of HIV RNA using the protocol described in Example 3 herein. Ct (cycle thresholds) values for protected Whatman® 903 papers soaked in Formulations 14, 15, 17, 18, 19, 20, 21, 22, 23, and 24 (Table 1) were compared with unprotected Whatman® 903 paper soaked in water (no formulation, NF 50° C.) and with unprotected Whatman® 903 paper soaked in water (no formulation, NF 25° C.) (see FIG. 5). The unprotected paper incubated at 25° C. (no formulation, NF 25° C.) served as reference with Ct values similar to a fresh sample (see FIG. 5).

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

Various embodiments of this application are described herein, including the best mode known to the inventors for carrying out the application. Variations on those embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention.

What is claimed is:

1. A solid matrix for storing a biological sample, comprising:
    a matrix material that is a non-dissolvable dry solid material;
    a buffer impregnated in the matrix material in a substantially dry state or a dry state; and
    at least one reducing agent and at least one antioxidant, but no denaturant or chelator;
    wherein the biological sample comprises one or more nucleic acids.

2. The solid matrix of claim 1, wherein the at least one reducing agent is impregnated in the matrix material in a substantially dry state.

3. The solid matrix of claim 2, wherein the at least one reducing agent is dithiothreitol (DTT), 2-mercaptoethanol (2-ME), 2-mercaptoethylamine, or cysteine.

4. The solid matrix of claim 1, wherein the at least one antioxidant is impregnated in the matrix material in a substantially dry state.

5. The solid matrix of claim 4, wherein the at least one antioxidant is hydroquinone monomethyl ether (MEHQ), hydroquinone (HQ), or toluhydroquinone (THQ).

6. The solid matrix of claim 1, wherein the non-dissolvable dry solid material is a cellulosic paper.

7. The solid matrix of claim 1, wherein the buffer is selected from citric acid, tris(2-carboxyethyl)phosphine hydrochloride (TCEP-HCl), oxidized form of tris(2-carboxyethyl)phosphine hydrochloride (TCEPO-HCl), 2-amino-2-hydroxymethyl-propane-1,3-diol (Tris), 2-(N-morpholino)ethanesulfonic acid (MES), 3-(N-morpholino)propanesulfonic acid (MOPS), 4-(2-hydroxyethyl)-1-piperazineethanesulfonic acid (HEPES), phosphate buffers, acetic acid, ascorbic acid, sulfosalicylic acid, formic acid, glycine, glycine-glycine, malic acid, and succinic acid.

8. The solid matrix of claim 1, wherein the buffer has a pH of 2.0 to 8.0.

9. The solid matrix of claim 1, wherein the biological sample is blood, serum, plasma, tissue, saliva, cells, synovial fluids, urine, or semen.

10. A method for storing one or more biological samples, the method comprising:
    contacting the solid matrix of claim 1 with a biological sample, wherein the biological sample comprises one or more nucleic acids;
    drying the solid matrix containing the biological sample; and
    storing the biological sample on the solid matrix in a substantially dry state or a dry state.

11. The method of claim 10, further comprising recovering the biological sample from the solid matrix.

12. The method of claim 11, further comprising extracting the nucleic acids from the biological sample.

13. The method of claim 10, wherein the nucleic acids are extracted from the biological sample and stored on the solid matrix in a substantially dry state or a dry state.

14. The method of claim 13, further comprising recovering the nucleic acids from the solid matrix.

15. The method of claim 10, wherein the non-dissolvable dry solid material is a cellulosic paper.

16. The method of claim 10, wherein the buffer is selected from citric acid, tris(2-carboxyethyl)phosphine hydrochloride (TCEP-HCl), oxidized form of tris(2-carboxyethyl)phosphine hydrochloride (TCEPO-HCl), 2-amino-2-hydroxymethyl-propane-1,3-diol (Tris), 2-(N-morpholino)ethanesulfonic acid (MES), 3-(N-morpholino)propanesulfonic acid (MOPS), 4-(2-hydroxyethyl)-1-piperazineethanesulfonic acid (HEPES), phosphate buffers, acetic acid, ascorbic acid, sulfosalicylic acid, formic acid, glycine, glycine-glycine, malic acid, and succinic acid.

17. The method of claim 10, wherein the buffer has a pH of 2.0 to 8.0.

18. The method of claim 10, wherein the biological sample is blood, serum, plasma, tissue, saliva, cells, synovial fluids, urine, or semen.

19. The method of claim 10, wherein the nucleic acids are RNA.

20. The method of claim 10, wherein the nucleic acids are virus RNA.

* * * * *